(12) United States Patent
Kirschenman

(10) Patent No.: US 9,402,555 B2
(45) Date of Patent: Aug. 2, 2016

(54) DRIVE ASSEMBLY FOR USE IN A ROBOTIC CONTROL AND GUIDANCE SYSTEM

(75) Inventor: Mark B. Kirschenman, Waverly, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 946 days.

(21) Appl. No.: 13/339,590

(22) Filed: Dec. 29, 2011

(65) Prior Publication Data

US 2013/0172713 A1    Jul. 4, 2013

(51) Int. Cl.
| | |
|---|---|
| *A61B 5/04* | (2006.01) |
| *A61M 25/092* | (2006.01) |
| *A61B 5/042* | (2006.01) |
| *A61M 25/01* | (2006.01) |

(52) U.S. Cl.
CPC ............ *A61B 5/042* (2013.01); *A61M 25/0113* (2013.01)

(58) Field of Classification Search
CPC ............................ A61B 5/042; A61M 25/0113
USPC ......... 604/95.01, 95.04; 606/1; 600/424, 374, 600/407, 423
See application file for complete search history.

(56) References Cited

U.S. PATENT DOCUMENTS

| | | | |
|---|---|---|---|
| 5,925,018 A | 7/1999 | Ungerstedt | |
| 6,096,004 A * | 8/2000 | Meglan ................. | A61B 34/75 604/95.01 |
| 6,233,476 B1 | 5/2001 | Strommer et al. | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,615,042 B2 * | 11/2009 | Beyar ................. | A61M 25/0113 600/106 |

(Continued)

FOREIGN PATENT DOCUMENTS

| | | |
|---|---|---|
| EP | 2797659 | 11/2014 |
| WO | 9639944 | 12/1996 |

(Continued)

OTHER PUBLICATIONS

An International Search Report for PCT Application No. PCT/US2012/026976, dated Jun. 29, 2012, 4 pgs.

(Continued)

*Primary Examiner* — Quynh-Nhu H Vu
(74) *Attorney, Agent, or Firm* — Dykema Gossett PLLC

(57) ABSTRACT

A drive assembly for use in a robotic control and guidance system comprises a cartridge having an outer housing and a rotatable medical device assembly disposed therein. The rotatable assembly includes a medical device having proximal and distal ends, and a housing having first and second ends, and a longitudinal axis extending therethrough. The proximal end of the medical device is disposed within the housing, and the housing further comprises an opening through which the medical device extends outwardly from said housing. The rotatable assembly further comprises a drive interface coupled with the housing. The drive assembly further comprises a manipulation base comprising a mounting plate onto which the cartridge is removably attached, and a drive system mounted to the mounting plate. The drive system is configured to operatively engage the cartridge drive interface and to impart rotational movement onto the rotatable assembly through the drive interface.

10 Claims, 13 Drawing Sheets

(56) References Cited

U.S. PATENT DOCUMENTS

| | | | |
|---|---|---|---|
| 7,998,020 B2 * | 8/2011 | Kidd | A61M 25/0113 476/19 |
| 2004/0254566 A1 * | 12/2004 | Plicchi | A61B 17/00 606/1 |
| 2006/0084911 A1 * | 4/2006 | Belef | A61B 8/12 604/95.01 |
| 2006/0264819 A1 * | 11/2006 | Fischer | A61M 25/0136 604/95.04 |
| 2008/0300592 A1 | 12/2008 | Weitzner et al. | |
| 2009/0247942 A1 * | 10/2009 | Kirschenman | 604/95.04 |
| 2009/0247993 A1 | 10/2009 | Kirschenman et al. | |
| 2009/0248042 A1 | 10/2009 | Kirschenman | |
| 2010/0204613 A1 * | 8/2010 | Rollins | A61M 25/09041 600/585 |
| 2010/0256558 A1 | 10/2010 | Olson et al. | |
| 2011/0015569 A1 | 1/2011 | Kirschenman et al. | |
| 2011/0028894 A1 | 2/2011 | Foley et al. | |
| 2011/0290855 A1 | 12/2011 | Moore et al. | |

FOREIGN PATENT DOCUMENTS

| | | |
|---|---|---|
| WO | 2009120982 A2 | 10/2009 |
| WO | 2011109283 | 9/2011 |

OTHER PUBLICATIONS

A Supplemental European Search Report for EP Application No. 12861400, dated Feb. 27, 2015, 5 pgs.

* cited by examiner

DRIVE ASSEMBLY FOR USE IN A ROBOTIC CONTROL AND GUIDANCE SYSTEM

BACKGROUND OF THE INVENTION a. Field of the Invention

The present disclosure relates generally to a robotic control and guidance system (RCGS) for one or more medical devices. More particularly, the present disclosure relates to a drive assembly for use in a RCGS that comprises, for example, a manipulation base and a medical device cartridge for a medical device, such as, for example, a spiral mapping catheter.

b. Background Art

Electrophysiology (EP) catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments.

In a typical EP procedure, a physician manipulates a catheter through a patient's vasculature to, for example, a patient's heart. The catheter typically carries one or more electrodes or sensors that may be used for mapping, ablation, diagnosis, and the like. Once at a target tissue site, the physician commences diagnostic and/or therapeutic procedures. Such procedures require precise control of the catheter during navigation, and delivery of therapy, to the target tissue site, which can invariably be a function of a user's skill level.

Robotic control and guidance systems (RCGS) for one or more medical devices (or robotically controlled medical device guidance systems) are known to facilitate such precise control. In general, these types of systems carry out (as a mechanical surrogate) input commands of a clinician or other end-user to deploy, navigate, and manipulate one or more medical devices, such as, for example, a catheter and/or an introducer or sheath for a catheter, or some other elongate medical instrument. One exemplary robotic catheter system is described and depicted in U.S. Patent Publication No. 2009/0247993 entitled "Robotic Catheter System," the entire disclosure of which is incorporated herein by reference.

While such systems have proved useful with respect to providing, among other benefits, precise control as described above, the particular use of an RCGS to perform mapping functions with certain medical devices (e.g., spiral mapping catheters) has proved complicated. This complexity is generally due to the fact that the these medical devices must be rotated into pulmonary veins. This presents a number of difficulties or issues. For example, one such issue relates to how a rotary or spiral catheter having multiple control actions (i.e., three-axis motion—translation, rotation, and the occlusion of the loop at the distal end of the device) and multiple sensors (e.g., electrodes), which, in some instances may number in upwards of twenty-four (24), can be manipulated without excessively complex mechanical or electrical interfacing.

Another issue relating to the use of an RCGS with a rotary or spiral medical device relates to how to shield the medical device and other components disposed in a sterile field (e.g., the table, drapes, the patient, etc.) from contaminants, and therefore, maintain sterility, when a non-sterile manipulating system is used.

Accordingly, the inventor herein has recognized a need for apparatus, such as, for example, a drive assembly and the constituent components thereof, for use with a RCGS that will minimize and/or eliminate one or more of the deficiencies in conventional systems.

BRIEF SUMMARY OF THE INVENTION

The present invention is directed to drive assembly for use in a robotic control and guidance system, and the constituent components thereof.

In accordance with one aspect of the invention and the present teachings, the drive assembly comprises a medical device cartridge and a manipulation base to which the cartridge is removably attached. In an exemplary embodiment, the drive assembly further includes a sterile barrier disposed between the cartridge and the manipulation base.

The cartridge of the drive assembly comprises an outer housing and a rotatable medical device assembly disposed within the outer housing. The rotatable medical device assembly, in turn, comprises an elongate medical device having a proximal end and a distal end, a housing within which a portion of the medical device is disposed, and a drive interface coupled with the housing.

More particularly, the a housing of the rotatable medical device includes a first end, a second end, and a longitudinal axis extending therethrough. The proximal end of the elongate medical device is disposed within the housing, and the housing further comprises an opening disposed in the first end thereof through which the elongate medical device extends outwardly from the housing in an axial direction relative to the longitudinal axis of the housing.

The manipulation base of the drive assembly comprises a mounting plate onto which the medical device cartridge is removably attached, and a drive system mounted to the mounting plate. The drive system comprises a rotary actuator and is configured to operatively engage the drive interface of the cartridge and to impart rotational movement onto the rotatable medical device assembly through the drive interface. In an exemplary embodiment, a portion of the outer housing of the cartridge comprises a base plate configured to be attached to the mounting plate of the manipulation base, and that has at least one aperture therein to facilitate the operative engagement of the drive interface of the cartridge with the drive system of the manipulation base. In an exemplary embodiment, the outer housing is configured to shield components disposed within the outer housing and/or in a field external thereto from contaminants.

The mounting plate of the manipulation base has a first side and a second side, and in an exemplary embodiment, the cartridge of the drive assembly is mounted to the first side, while the drive system of the manipulation base is mounted to the second side.

In an exemplary embodiment, the cartridge of the drive assembly further comprises an electrical port disposed in the housing of the rotatable medical device assembly. The port has a first end that is configured to be electrically coupled with a lead wire of a sensor associated with the elongate medical device, and a second end external to the housing of the rotatable medical device assembly that is configured to be electrically coupled with a complementary electrical connector. In an exemplary embodiment, the manipulation base of the drive assembly further comprises a commutator mounted on the mounting plate thereof proximate the cartridge. The commutator has a first electrical connector that may be electrically coupled to the second end of the port of the cartridge, and a second electrical connector configured for coupling with a complementary electrical connector of an electrical cable.

In an exemplary embodiment, the drive interface of the cartridge, and the rotatable medical device assembly thereof, in particular, is a first drive interface, and the drive system of the manipulation base is a first drive assembly. Further, the medical device comprises a steering wire and the rotatable medical device assembly comprises a control member, such as, for example, a slider block, disposed within the housing thereof and rigidly coupled with the steering wire of the medical device. The control member is configured for translational movement relative to the longitudinal axis of the housing. In such an embodiment, the cartridge further comprises a second drive interface coupled with the control member, and the manipulation base further comprises a second drive system mounted to said mounting plate. The second drive system comprises an electromechanical device and is configured to operatively engage the second drive interface of the cartridge and to impart translational movement onto the control member through the second drive interface.

In accordance with another aspect of the invention and the present teachings, a manipulation base for use with a medical device cartridge in a robotically controlled medical device guidance system is provided. The manipulation base comprises a mounting plate configured to have a medical device cartridge removably attached thereto and defines a longitudinal axis. The manipulation base further comprises a drive system mounted to the mounting plate, wherein the drive system comprises a rotary actuator and is configured to operatively engage a drive interface of the cartridge and to impart rotational movement onto the drive interface of the cartridge. The rotary actuator may comprise a motor, and the drive interface may further comprise one of a motor-driven friction interface and a motor-driven gear arrangement.

In an exemplary embodiment, the drive system of the manipulation base is a first drive system, and the drive interface of the cartridge is a first drive interface. In such an embodiment, the manipulation base further comprises a second drive system mounted to the mounting plate. The second drive system comprises an electromechanical device and is configured to operatively engage a second drive interface of the cartridge, and to impart translational movement onto the second drive interface. The electromechanical device may comprise, for example, a motor and one of a motor-driven ball screw and a motor-drive lead screw. Further, the second drive system may comprise a driven member, which in an exemplary embodiment is a drive fork, configured to operatively engage the second drive interface of the cartridge and to be drive by the electromechanical device. The driven member may further include a roller disposed therein that is configured to operatively engage the second drive interface of the cartridge to facilitate rotation of the second drive interface. In an exemplary embodiment, the second drive system further comprises a force sensor that is configured for mechanically isolated sensing of the force applied by the second drive system onto the second drive interface. The force sensor may comprise a strain gauge or a motor current sensor. In an exemplary embodiment, the driven member of the second drive system is coupled to the electromechanical device by the force sensor. Further, the manipulation base may comprise a bearing block associated with the driven member and a bearing rail, wherein the bearing block is configured to travel along the bearing rail as the driven member is driven by the electromechanical device.

In an exemplary embodiment, the manipulation base still further comprises a commutator mounted on the mounting plate. The commutator has a first electrical connector configured to be electrically connected to an electrical port of the cartridge to thereby electrically connect the commutator to at least one sensor of the elongate medical device that is electrically connected to the electrical port. The commentator further comprises a second electrical connector configured for coupling the commutator with a complementary electrical connector of an electrical cable.

In accordance with another aspect of the invention, a medical device cartridge for use in a robotically controlled medical device guidance system is provided. The cartridge comprises an outer housing and a rotatable medical device assembly disposed within the outer housing. The rotatable medical device assembly comprises an elongate medical device having a proximal and a distal end, and in an exemplary embodiment, one or more steering wires. In an exemplary embodiment, the elongate medical device may further comprise one or more force sensors disposed therein configured to measure, for example, the force applied to the steering wire(s) thereof. The rotatable medical device assembly further comprises a housing having a first end, a second end, and a longitudinal axis extending therethrough. The proximal end of the medical device is disposed within the housing, and the housing comprises an opening disposed in the first end thereof through which the medical device extends outwardly from the housing in an axial direction relative to the longitudinal axis of the housing. The rotatable assembly further comprises a drive interface coupled with the housing and configured to be operatively engaged with a drive system of a manipulation base to impart rotational movement onto the rotatable assembly about the longitudinal axis of the housing.

In an exemplary embodiment, the outer housing of the cartridge comprises a first portion having an opening therein that is coaxially arranged with the opening in the housing of the rotatable assembly such that the elongate medical device extends outwardly from the outer housing of the cartridge. The outer housing may further comprise a second portion comprising a base plate of the cartridge that is configured to permit the cartridge to be removably attached to the manipulation base, and that had at least one aperture therein configured to permit the operative engagement of the drive interface with the drive system of the manipulation base. In an exemplary embodiment, the outer housing is configured to shield components disposed within the outer housing and/or in a field external thereto from contaminants.

In an exemplary, the drive interface of the rotatable medical device assembly is configured to be operatively engaged with the drive system of said manipulation base that is axially-arranged with the rotatable medical device assembly relative to the longitudinal axis of the housing thereof. In another exemplary embodiment, the drive interface is configured to be operatively engaged with the drive system of the manipulation base that is disposed below the rotatable medical device assembly (i.e., disposed below the longitudinal axis of the housing of the rotatable medical device assembly).

In an exemplary embodiment, the drive interface of the rotatable assembly is a first drive interface configured to be operatively engaged with a first drive system of the manipulation base. In such an embodiment, the rotatable medical device assembly may further comprise a control member, such as, for example, a slider block, disposed with the housing thereof and rigidly coupled with a steering wire of the medical device. The control member is configured to translational movement relative to the longitudinal axis of the housing. The rotatable medical device assembly may still further comprise a second drive interface coupled with the control member and configured to be operatively engaged with a second drive system of the manipulation base to impart translational movement onto the control member. In an exemplary embodiment, the housing of the rotatable assembly includes an axially extending slot therein, and the control member includes a pin extending therefrom in a radial direction relative to the longitudinal axis. The pin is disposed and configured for travel within the slot in an axial direction relative to the longitudinal axis, and the second drive interface is coupled with the pin.

In an exemplary embodiment, the control member of the rotatable medical device assembly is a first control member, and the steering wire coupled thereto is a first steering wire of the medical device. In such an embodiment, the rotatable assembly further comprises a second control member, such as, for example, a slider block, disposed within the housing thereof and rigidly coupled to a second steering wire of the medical device. The second control member is configured for translational movement relative to the longitudinal axis of the housing. The rotatable assembly may further comprise a third drive interface coupled with the second control member and configured to be operatively engaged with a third drive system of the manipulation base to impart translational movement onto the second control member. In an exemplary embodiment, the housing of the rotatable assembly includes an axially extending slot therein, and the second control member includes a pin extending therefrom in a radial direction relative to the longitudinal axis. The pin is disposed and configured for travel within the slot in an axial direction relative to the longitudinal axis, and the third drive interface is coupled with the pin.

In accordance with yet another aspect of the invention, a rotatable medical device assembly for use in a medical device cartridge of a robotically controller medical device guidance system is provided. The rotatable assembly comprises an elongate medical device having a proximal and a distal end. The rotatable assembly further comprises a housing having a first end and a second end, and a longitudinal axis extending therethrough. The proximal end of the medical device is disposed within the housing, and the housing further comprises an opening disposed in the first end thereof through which the medical device extends outwardly from the housing in an axial direction relative to the longitudinal axis of the housing.

In an exemplary embodiment, the rotatable assembly further comprises an anchor member disposed within said housing and rigidly coupled with the proximal end of the medical device.

The rotatable housing may further comprise an electrical port disposed within the housing. The port comprises a first end and a second end, wherein the first end is configured to be electrically coupled with a lead wire of a sensor of the medical device, and the second end is disposed external to the housing and configured to be electrically coupled with a complementary electrical connector.

In an exemplary embodiment, the drive interface of the rotatable assembly is a first drive interface configured to be operatively engaged with a first drive system of the manipulation base, and the medical device comprises at least one steering wire. In such an embodiment, the rotatable assembly further comprises a control member disposed with the housing and rigidly coupled with a steering wire of the medical device. The control member is configured for translational movement relative to the longitudinal axis of the housing. The rotatable assembly further comprises a second drive interface coupled with the control member and configured to be operatively engaged with a second drive system of the manipulation base to impart translational movement onto the control member. In an exemplary embodiment, the housing of rotatable assembly has an axially extending slot therein, and the control member includes a pin extending therefrom in a radial direction relative to the longitudinal axis of the housing. The pin is disposed and configured for travel within the slot in an axial direction relative to the longitudinal axis, and the second drive interface is coupled with the pin.

In an exemplary embodiment, the control member is a first control member and the steering wire coupled thereto is a first steering wire. In such an embodiment. The rotatable assembly further comprises a second control member disposed with the housing and rigidly coupled to a second steering wire of the medical device. The second control member is configured for translational movement relative to the longitudinal axis of the housing. The rotatable assembly may further comprise a third drive interface coupled with the second control member and configured to be operatively engaged with a third drive system of the manipulation base to impart translation movement onto the second control member. In such an embodiment, the housing may further include an axially extending slot therein, and the second control member may include a pin extending therefrom in a radial direction relative to the longitudinal axis. The pin is disposed and configured for travel within the slot in an axial direction relative to the longitudinal axis, and the third drive interface is coupled with the pin.

The foregoing and other aspects, features, details, utilities, and advantages of the present disclosure will be apparent from reading the following description and claims, and from reviewing the accompanying drawings.

DETAILED DESCRIPTION OF THE INVENTION

Before proceeding to a detailed description of a drive assembly for use in a robotically controlled guidance system (RCGS), a brief overview (for context) of an exemplary RCGS for manipulating one or more medical devices will first be provided. The description of the RCGS will, in general terms, detail the various components of an exemplary RCGS. Following that description, the present specification will describe the drive assembly for use in an RCGS.

Exemplary RCGS System Description.

Figure 1:
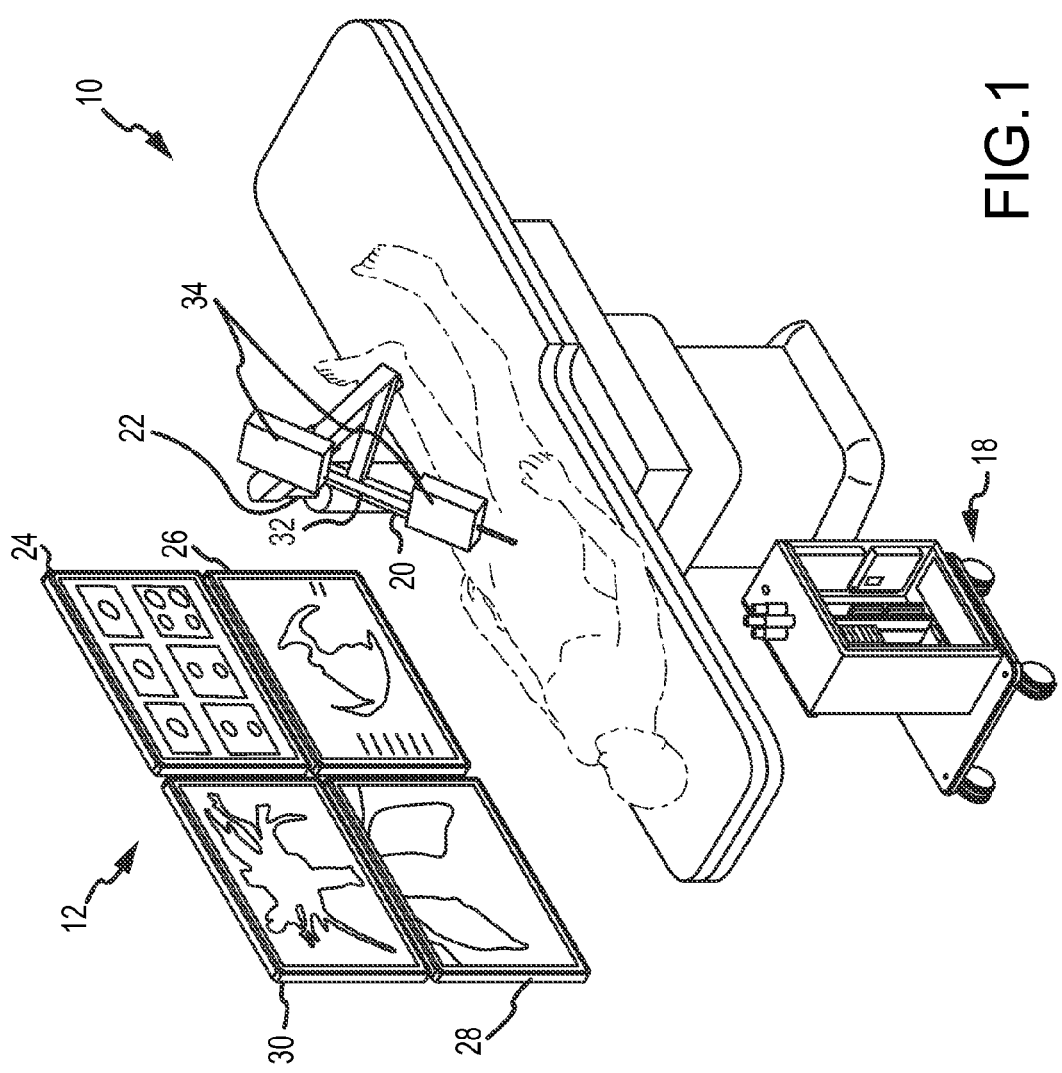
FIG. 1 is an isometric diagrammatic view of a robotic control and guidance system, and a robotically controlled medical device guidance system, in particular, illustrating an exemplary layout of various system components.

Referring now to the drawings wherein like reference numerals are used to identify identical components in the various views, FIG. 1 illustrates one exemplary embodiment of a robotic control and guidance system 10 (RCGS 10) for manipulating one or more medical devices. The RCGS 10 can be used, for example, to manipulate the location and orientation of catheters, such as, for example, mapping catheters, and sheaths in a heart chamber or in another body cavity or lumen. The RCGS 10 thus provides the user with a similar type of control provided by a conventional manually-operated system, but allows for repeatable, precise, and dynamic movements. For example, a user such as an electrophysiologist can identify locations (potentially forming a path) on a rendered computer model of the cardiac anatomy. The system can be configured to relate those digitally selected points to positions within a patient's actual/physical anatomy, and can thereafter command and control the movement of the sheath and/or catheter to the defined positions. Alternatively, a user can remotely control the movement of the sheath and/or catheter to a desired position within the patient's anatomy. In any event, once at the specified target position, either the user or the system can perform the desired diagnostic or therapeutic function. The RCGS 10 enables full robotic navigation/guidance and control.

As shown in FIG. 1, the RCGS 10 can generally include one or more monitors or displays 12, a visualization, mapping, and/or navigation system 14, a human input device and control system (referred to as "input control system") 16, an electronic control system 18, a manipulator assembly (or head assembly) 20, and a manipulator assembly support structure 22 for positioning the manipulator assembly 20 in proximity to a patient or a patient's bed.

The displays 12 are configured to visually present to a user information regarding patient anatomy, medical device location or the like, originating from a variety of different sources. The displays 12 can include, for example: a monitor 24 (coupled to system 14—described more fully below) for displaying cardiac chamber geometries or models, displaying maps and activation timing and voltage data to identify arrhythmias, and for facilitating guidance of catheter movement; a fluoroscopy monitor 26 for displaying a real-time x-ray image or for assisting a physician with catheter movement; an intra-cardiac echo (ICE) display 28 to provide further imaging; and an EP recording system display 30.

The visualization, navigation, and/or mapping system 14 is configured to provide many advanced features, such as visualization, mapping, navigation support and positioning (i.e., determine a position and orientation (P&O) of a sensor-equipped medical device, for example, a P&O of a distal tip portion of a catheter). In an exemplary embodiment, the system 14 may comprise an impedance-based system, such as, for example, the EnSite NavX™ system commercially available from St. Jude Medical, Inc., and as generally shown by reference to U.S. Pat. No. 7,263,397 entitled "Method and Apparatus for Catheter Navigation and Location and Mapping in the Heart," the entire disclosure of which is incorporated herein by reference. In other exemplary embodiments, however, the system 14 may comprise other types of systems, such as, for example and without limitation: a magnetic-field based system such as the Carto™ System available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; and a combination impedance-based and magnetic field-based system such as the Carto 3™ System also available from Biosense Webster.

As briefly described above, in an exemplary embodiment, the system 14 involves providing one or more positioning sensors for producing signals indicative of medical device location (position and/or orientation) information. In an embodiment wherein the system 14 is an impedance-based system, the sensor(s) may comprise one or more electrodes. Alternatively, in an embodiment wherein the system 14 is a magnetic field-based system, the sensor(s) may comprise one or more magnetic sensors (e.g., coils) configured to detect one or more characteristics of a low-strength magnetic field.

The input control system 16 is configured to allow a user, such as an electrophysiologist, to interact with the RCGS 10, in order to control the movement and advancement/withdrawal of one or more medical devices, such as, for example, a catheter and/or a sheath (see, e.g., U.S. Patent Publication No. 2010/0256558 entitled "Robotic Catheter System," and PCT/US2009/038597 entitled "Robotic Catheter System with Dynamic Response," published as WO 2009/120982, the entire disclosures of which are incorporated herein by reference). Generally, several types of input devices and related controls can be employed, including, without limitation, instrumented traditional catheter/sheath handle controls, oversized catheter/sheath models, instrumented user-wearable gloves, touch screen display monitors, 2-D input devices, 3-D input devices, spatially detected styluses, and traditional joysticks. For a further description of exemplary input apparatus and related controls, see, for example, U.S. Patent Publication Nos. 2011/0015569 entitled "Robotic System Input Device" and 2009/0248042 entitled "Model Catheter Input Device," the entire disclosures of which are incorporated herein by reference. The input devices can be configured to directly control the movement of the catheter and sheath, or can be configured, for example, to manipulate a target or cursor on an associated display.

The electronic control system 18 is configured to translate (i.e., interpret) inputs (e.g., motions) of the user at an input device of the input control system 16 (or from another source) into a resulting movement of one or more medical devices (e.g., a catheter and/or a sheath). In this regard, the system 18 includes a programmed electronic control unit (ECU) in communication with a memory or other computer readable media (memory) suitable for information storage. Relevant to the present disclosure, the electronic control system 18 is configured, among other things, to issue commands (i.e., actuation control signals) to the manipulator assembly 20, and as will be described in greater detail below, to the drive assemblies thereof, in particular, to move or bend the medical device(s) associated therewith to prescribed positions and/or in prescribed ways, all in accordance with the received user input and/or a predetermined operating strategy programmed into the system 18. In addition to the instant description, further details of a programmed electronic control system can be found in U.S. Patent Publication No. 2010/0256558, the entire disclosure of which was incorporated herein by reference above. It should be understood that although the visualization, navigation, and/or mapping system 14 and the electronic control system 18 are shown separately in FIG. 1, integration of one or more computing functions can result in a system including an ECU on which can be run both (i) various control and diagnostic logic pertaining to the RCGS 10 and (ii) the visualization, navigation, and/or mapping functionality of system 14.

Generally speaking, the manipulator assembly 20, in response to commands issued by the electronic control system 18, is configured to maneuver the medical device(s) associated therewith (e.g., translation movement, such as advancement and withdrawal of the medical device(s)), as well as to effectuate distal end (tip) deflection and/or rotation. More particularly, in an embodiment, the manipulator assembly 20 can include a translation assembly 32 and one or more drive assemblies 34 mounted to said translation assembly 32. Each drive assembly 34 corresponds to a respective medical device that is to be controlled by the RCGS 10, and is configured to manipulate or maneuver the medical device in response to commands issued by the electronic control system 18. More specifically, in the exemplary embodiment illustrated in FIG. 1, the manipulator assembly 20 may include a pair of drive head assemblies 34—one configured to manipulate or maneuver a sheath associated therewith, and the other configured to manipulate or maneuver a catheter associated therewith. In such an embodiment, the drive head assemblies 34, as well as the translation assembly 32, may operate together to maneuver the respective medical devices.

As further illustrated in FIG. 1, and as briefly described above, the RCGS 10 may further include a support structure 22 for supporting the head assembly 20. The structure 22 can generally include a support frame including an attachment assembly for attachment to an operating bed. A plurality of support linkages can be provided for accurately positioning one or more manipulator assemblies, such as the manipulator assembly 20. In another exemplary embodiment, the support structure 22 may further include wheels to allow for the support structure 22, and if mounted thereon, the manipulator assembly 20, to be easily moved.

Drive Assembly.

Figure 2:
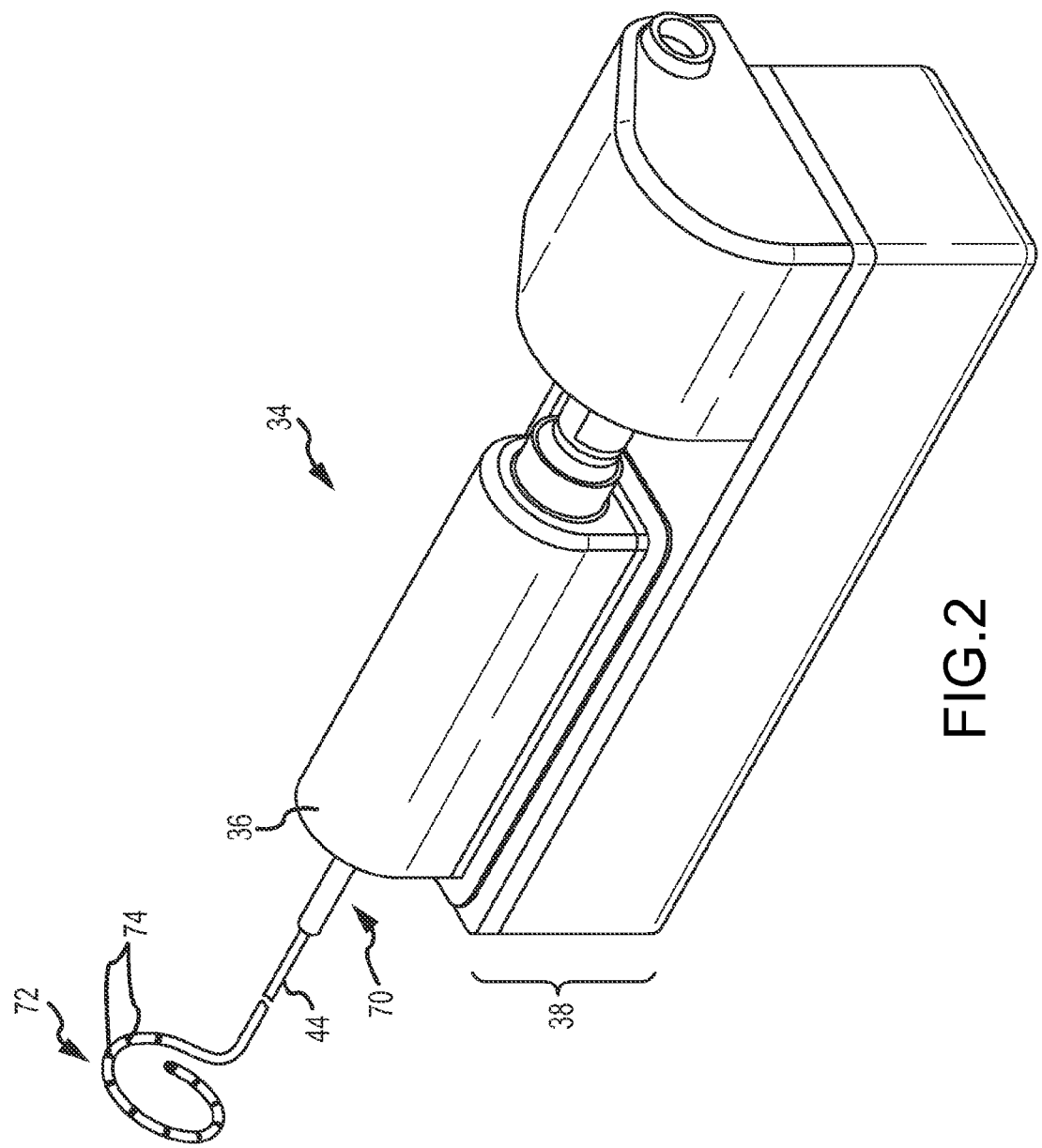
FIG. 2 is an isometric view of an exemplary drive assembly for use in a robotic control and guidance system such as that illustrated in FIG. 1.

With reference to FIG. 2, in an exemplary embodiment, the drive assembly 34 comprises a medical device cartridge 36 for an elongate medical device, such as, for example, a sheath or a catheter (e.g., a spiral mapping catheter), and a manipulation base 38. As will be described in greater detail below, the cartridge 36 and the manipulation base 38 are each configured to allow the cartridge 36 to be removably attached to the manipulation base 38.

Figure 3:
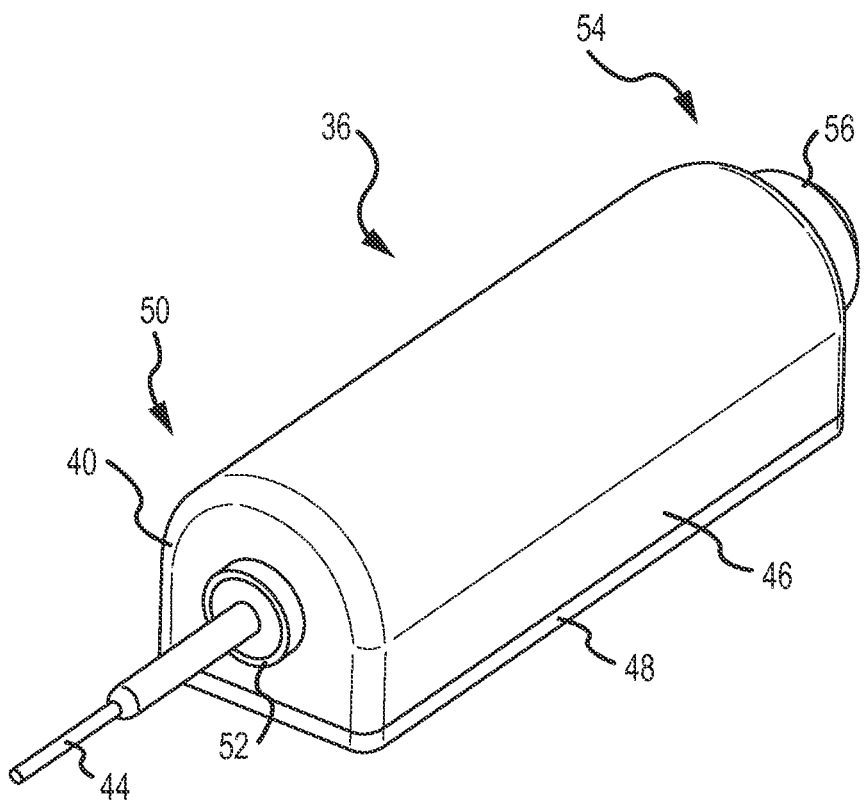
FIG. 3 is an isometric view of an exemplary medical device cartridge of the drive assembly illustrated in FIG. 2.
Figure 4:
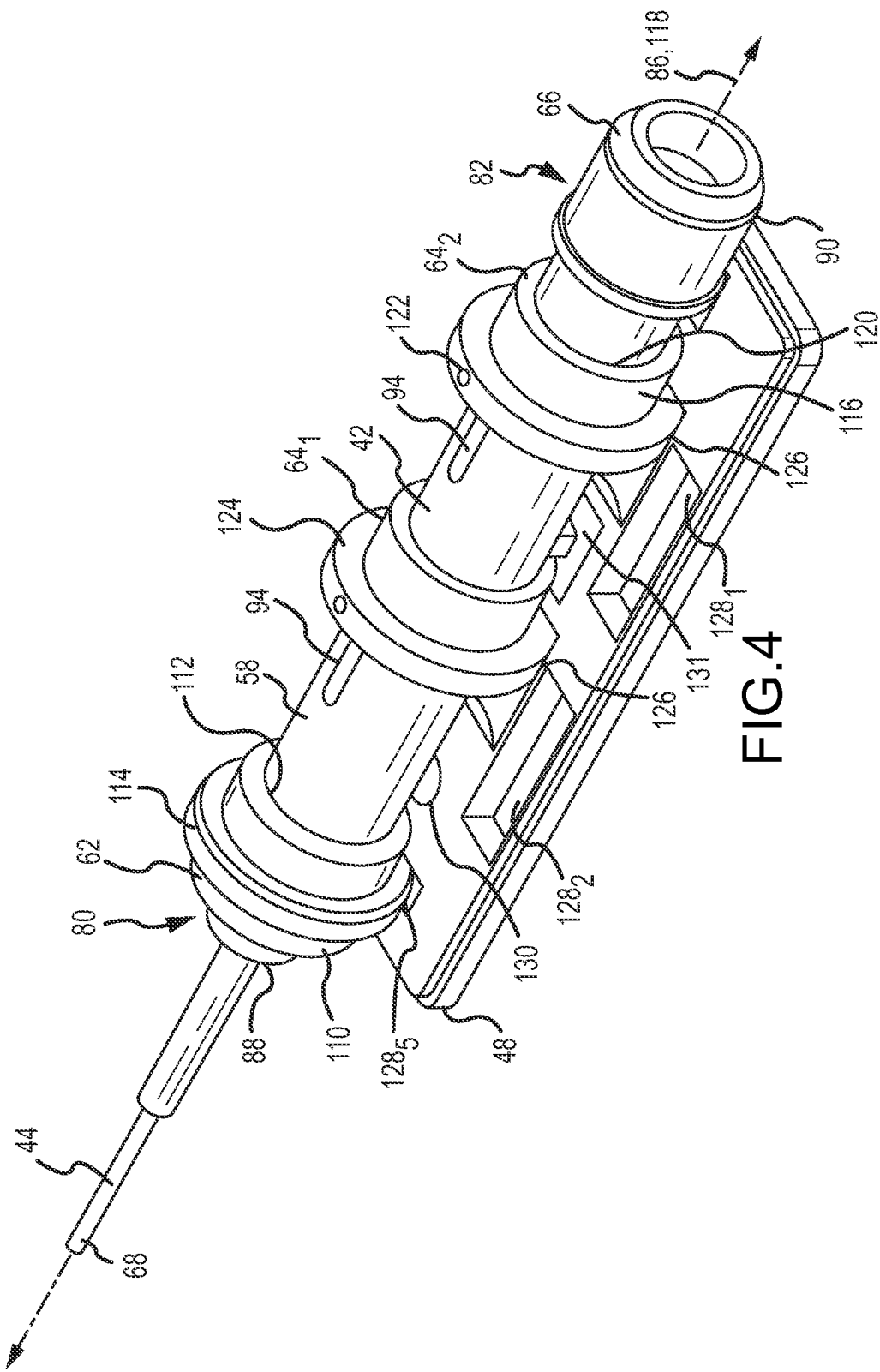
FIG. 4 is an isometric view of the cartridge illustrated in FIG. 3 with a portion of the outer housing thereof to show the exemplary cartridge in greater detail.

With reference to FIGS. 3 and 4, in an exemplary embodiment, the cartridge 36 comprises an outer housing 40 and a rotatable medical device assembly 42 (or rotatable assembly 42) disposed within the outer housing 40 and comprising, among other components, an elongate medical device 44. In an exemplary embodiment, some or all of the components of the cartridge 36 are disposable.

As illustrated in FIG. 3, the outer housing 40 is configured to house the rotatable assembly 42, and is further configured shield the medical device 44 and other components disposed in a sterile field that is external to the outer housing 40 (e.g., the patient table, drapes, the patient, etc.) from contaminants, and therefore, to help maintain sterility. In an exemplary embodiment, the outer housing 40 is comprised of multiple pieces that can be coupled together. For example, in an exemplary embodiment, the housing 40 comprises a first, or top portion 46, and a second, or bottom portion 48. The first and second portions 46, 48 are configured to interface with each other to allow the first portion 46 to be detachably coupled with the second portion 48. The first and second portions 46, 48 may be detachably coupled using any number of techniques known in the art. For example, the first and second portions 46, 48 may be coupled by an interference or press fit. In another exemplary embodiment, the portions 46, 48 may be coupled by complementary interlocking members disposed on each portion. In still other exemplary embodiments, conventional fasteners or any other techniques described elsewhere herein or known in the art, may be used. In an exemplary embodiment, the first and second portions 46, 48 are formed of plastic, although the present disclosure is not meant to be so limited.

With continued reference to FIG. 3, in an exemplary embodiment, the first portion 46 has a first end 50 having a first opening 52 disposed therein, and a second end 54 having a second opening 56 disposed therein. In an exemplary embodiment, the openings 52, 56 are flanged openings. The openings 52, 56 are configured to receive and support respective portions of the rotatable assembly 42, and to allow the rotatable assembly 42 to rotate therein. Further, and as will be described in greater detail below, in an exemplary embodiment, the second portion 48 comprises a base plate configured, in part, to allow the cartridge 36 to be removably attached to the manipulation base 38.

It will be appreciated that while only a two-piece outer housing is described with particularity herein, in other exemplary embodiments the housing 40 may comprise more or less than two pieces, and such embodiments remain within the spirit and scope of the present disclosure.

Figure 5:
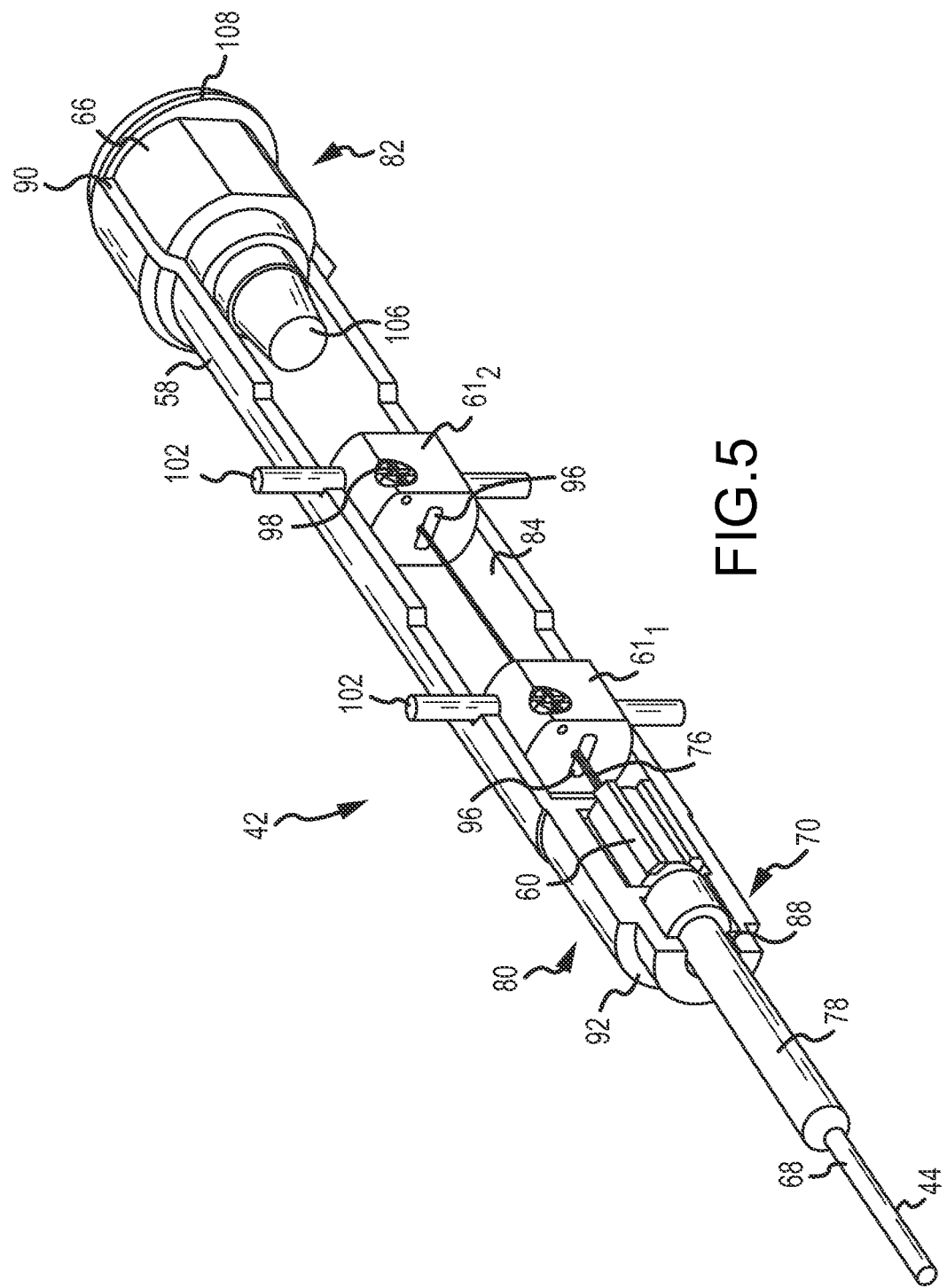
FIG. 5 is an isometric view of an exemplary rotatable medical device assembly of the cartridge illustrated in FIGS. 3 and 4, wherein a portion of the housing thereof has been removed to show the exemplary rotatable assembly in greater detail.

FIGS. 4 and 5 depict an exemplary embodiment of the rotatable assembly 42 of the cartridge 36. In addition to the medical device 44, in an exemplary embodiment, the rotatable assembly 42 further comprises a housing 58 configured, in part, to retain a portion (proximal end) of the medical device 44, an anchor member 60 disposed within housing 58, and one or more slider blocks 61 also disposed with the housing 58. In an exemplary embodiment, the rotatable assembly 42 may further comprise one or more mechanical drive interfaces 62 configured to be operatively engaged with corresponding drive systems of the mounting base 38 to impart rotational movement onto the rotatable assembly 42; and one or more mechanical drive interfaces 64 configured to be operatively engaged with corresponding drive systems of the mounting base 38 to impart translational movement onto the one or more slider blocks 61 of the rotatable assembly 42. The rotatable assembly 42 may still further comprise an electrical port 66 disposed in the housing 58 thereof. As will be described below, in an exemplary embodiment, the rotatable assembly 42 is configured to be supported by, and to rotate within, the flanged openings 52, 56 of the housing 40.

As briefly described above, the rotatable assembly 42 comprises an elongate medical device 44. The medical device 44 may comprise either a sheath or a catheter, and more specifically, a rotary or spiral medical device, such as, for example, a spiral mapping catheter. In any event, the medical device 44 comprises a shaft 68 having a proximal end 70 and a distal end 72 (best shown in FIG. 2). As will be described below, the proximal end 70 is disposed and retained within the housing 58 of the rotatable assembly 42. The medical device 44 may further comprise one or more sensors 74 disposed at or near the distal end 72 that may be used for a variety of diagnostic and/or therapeutic purposes including, for example, EP studies, mapping, catheter identification and location, pacing, ablation, and the like. Each sensor 74 includes at least one lead wire (not shown) electrically connected thereto and extending therefrom to the proximal end 70 of the shaft 68. In an exemplary embodiment, the lead wire(s) for each sensor 74 are electrically connected to the electrical port 66, as will be described in greater detail below. Accordingly, in such an embodiment, the lead wire(s) are routed through the housing 58 of the rotatable assembly 42 and terminate at the electrical port 66. As briefly described above, the medical device 44 may comprise a device configured to perform a mapping function (e.g., a spiral mapping catheter), or may comprise any number of other medical devices, such as, for example, intracardiac echocardiography (ICE) catheters, catheters for use in high-intensity focused ultrasound (HIFU) ablation systems, or any other medical devices used in diagnostic or therapy delivery systems (e.g., ablation systems, drug delivery systems, etc.) that require the medical device, or components thereof, to be focused in a given direction.

As is well known in the art, the medical device 44 may further comprise one or more steering wires 76 disposed within the shaft 68 and configured to cause the shaft 68 to deflect. For purposes of illustration, the description below will be limited to an embodiment wherein the medical device 44 comprises two steering wires 76 (steering wires 76$_1$, 76$_2$). It will be appreciated, however, that the present disclosure is not meant to be limited to such an embodiment, but rather embodiments wherein the medical device 44 comprises more or less than two steering wires remain within the spirit and scope of the present disclosure. Each steering wire 76 has a proximal end and a distal end. The distal end of the steering wire 76 is rigidly coupled to a mounting structure disposed within the shaft 68 of the medical device 44, such as, for example, a pull ring. The proximal end, as will be described below, is rigidly coupled to a control member disposed within the housing 58 of the rotatable assembly 42.

As illustrated in FIGS. 4 and 5, in order to avoid buckling of the proximal end of the shaft 68 as a result of forces applied thereto during use, in an exemplary embodiment, the medical device 44 further comprises a stiffening tube or strain relief 78 affixed to or joined with the shaft 68 at or near the proximal end 70 thereof. In an exemplary embodiment, the stiffening tube 78, which may be formed of plastic, is disposed at such a location on the shaft 68 that one portion of the tube 78 extends into the housing 58 of the rotatable assembly 42, while another portion extends external to the housing 58.

With continued reference to FIGS. 4 and 5, the housing 58 of the rotatable assembly 42 has a first end 80, a second end 82, and a cavity 84. The housing 58 further defines a longitudinal axis 86 extending through both the first and second ends 80, 82 thereof. In an exemplary embodiment, the housing 58 is configured such that when the cartridge 36 is assembled, the first end 70 thereof is disposed within and supported by the flanged opening 52 of the housing 40, and the second end 82 thereof is disposed within and supported by the flanged opening 56 of the housing 40. For reasons that will be described in greater detail below, the housing 58 may further include a first opening 88 disposed in the first end 80 thereof, and a second opening 90 disposed in the second end 82 thereof. The housing 58 is configured to, among other things, shield the components disposed therein from contaminants so as to help maintain the sterility of, for example, the medical device 44.

As illustrated in FIG. 4, in an exemplary embodiment, the housing 58 has a substantially tubular shape. In such an embodiment, the housing 58 may have a constant outer diameter from the first end 80 thereof to the second end 82, or different portions of the housing 58 may have different outer diameters. For example, as illustrated in FIG. 5, a center portion of the housing 58 may have a first outer diameter, while a portion of the housing 58 at the first end 80 thereof may have a second outer diameter that is less than the first outer diameter, and a portion of the housing 58 at the second end 82 thereof may have a third outer diameter that is larger than both the first and second outer diameters. In an exemplary embodiment, such as that illustrated in FIG. 5, a first portion of the housing 58 at the first end 80 thereof may have an outer diameter sized to allow the first end 80 of the housing 58 to be disposed within the flanged opening 52 of the outer housing 40. In such an embodiment, an adjacent portion of the housing 58 may have a larger outer diameter so as to form a shoulder 92 where the housing 58 transitions between the two portions having different diameters. The shoulder 92 may serve a positioning or orienting function when, in an embodiment, the first end 80 of the housing 58 is inserted into and/or disposed within the flanged opening 52 in the housing 40. Similarly, a second portion of the housing 58 at the second end 82 thereof may have an outer diameter sized to allow the second end 82 to be disposed within the flanged opening 56 of the outer housing 40.

As with the outer diameter, the housing 58 may also have a constant inner diameter throughout its length, or different portions of the housing 58 may have different inner diameters. For example, as illustrated in FIG. 5, a center portion of the housing 58 may have a first inner diameter, while a portion of the housing 58 at the first end 80 thereof may have a second inner diameter that is less than the first inner diameter, and a portion of the housing 58 at the second end 82 thereof may have a third inner diameter that is larger than both the first and second inner diameters.

While both the housing 58 and the cavity 84 thereof have thus far been described and depicted as having a circular cross-section, it will be appreciated that in other embodiments one or both of the housing 58 and the cavity 84 may have a cross-sectional shape other than circular, and such embodiments remain within the spirit and scope of the present disclosure.

As illustrated in FIGS. 4 and 5, in an exemplary embodiment, and for reasons that will be described in greater detail below, the housing 58 further comprises one or more slots 94 therein extending along the length of the housing 58 in an axial direction relative to the longitudinal axis 86. In an exemplary embodiment, the housing 58 has a plurality of axially extending slots 94. For example, the housing 58 may comprise a pair of slots 94. In such an embodiment, the slots 94 may be linearly aligned or co-linear with each other (as illustrated in FIG. 4, for example). In another exemplary embodiment, the slots 94 may be diametrically opposed (i.e., disposed in different sides or portions of the housing 58 but in vertical alignment). In still another exemplary embodiment, the housing 58 may comprise four axially extending slots 94. In such an embodiment, two of the slots 94 may be linearly aligned with each other, while the second pair of slots 94 may also be linearly aligned with each other but diametrically opposed to the first pair of slots 94. Accordingly, it will be appreciated that the housing 58 may include any number of axially-extending slots 94, and therefore, embodiments of the housing 58 having more or less slots 94 than described herein remain within the spirit and scope of the present disclosure.

The housing 58 may be of a unitary construction or, alternatively, may be formed of multiple pieces that when coupled together form the housing 58. For example, in an exemplary embodiment, the housing 58 is comprised of two pieces that are configured to be detachably coupled together. The two pieces may be detachably coupled using any number of techniques well known in the art, such as, for example, those described above with respect to the coupling of the first and second portions 46, 48 of the housing 40. In addition, or alternatively, the pieces forming the housing 58 may be held together by other components of the rotatable assembly 42, such as, for example, the drive interfaces 62, 64 described below and illustrated in FIG. 4. In an exemplary embodiment, each piece forming the housing 58, and therefore, the housing 58 itself, is formed of plastic, although the present disclosure is not meant to be so limited.

With continued reference to FIG. 5, and as briefly described above, the rotatable assembly 42 further comprises an anchor member 60. The anchor member 60 is configured to receive and retain the proximal end 70 of the medical device 44. The anchor member 60 is disposed within the cavity 84 of the housing 58 at the first end 80 thereof. The anchor member 60 is further disposed proximate the first opening 88 in the first end 80 of the housing 58, which is sized and configured to allow the medical device 44 to extend outwardly from the housing 58 in an axial direction relative to the longitudinal axis 86. Accordingly, the medical device 44 extends from the anchor member 60 and out through the opening 88 in the housing 58. Therefore, and as illustrated in FIG. 2, when the first end 80 of the rotatable assembly 42 is disposed within the flanged opening 52 in the cartridge outer housing 40, the opening 52 allows the medical device 44 to extend outwardly from the cartridge outer housing 40.

In an exemplary embodiment, the anchor member 60 includes a passageway (not shown) therein that permits components of the medical device 44, such as, for example, sensor lead wires and steering wires 76, to pass therethrough for purposes that will be described in greater detail below. The anchor member 60 may be arranged such that the passageway is coaxial to the longitudinal axis 86 of the housing 58. The anchor member 60 may be held or restrained in place in a number of ways. For example, in an exemplary embodiment, the anchor member 60 is sized such that when the rotatable assembly 42 is assembled, the outer surface of the anchor member 60 is in contact or near contact with the inner surface of the cavity 84, and therefore, the housing 58 of the rotatable assembly 42 holds the anchor member 60 in place. In addition, or alternatively, conventional fasteners and/or adhesives may be used. In an exemplary embodiment, the anchor member 60 is formed of plastic, however, the present disclosure is not meant to be so limited.

As briefly described above, the rotatable assembly 42 still further comprises at least one or more control members or slider blocks 61. For purposes of illustration and clarity, the description below will be limited to an embodiment wherein the rotatable assembly 42 comprises two slider blocks 61 (slider blocks $61_1$, $61_2$). It will be appreciated, however, that depending on the particular medical device 44, the rotatable assembly 42 may comprise one, more than two, or no slider blocks 61. Therefore, embodiments wherein the rotatable assembly 42 comprises more or less than two slider blocks 61 remain within the spirit and scope of the present disclosure.

As illustrated in FIG. 5, the slider blocks 61 are disposed within the cavity 84 of the housing 58. Each slider block 61 is configured to be rigidly coupled with a respective steering wire 76 of the medical device 44 and for translational movement within the cavity 84 relative to the longitudinal axis 86 of the housing 58. Accordingly, the slider block $61_1$ is configured to be coupled with a first steering wire $76_1$, and the slider block $61_2$ is configured to be coupled to a second steering wire $76_2$. In an exemplary embodiment, each slider block 61 has a passageway or channel 96 disposed therein. As with the anchor member 60 described above, the passageway 96 permits components of the medical device 44, such as, for example, sensor lead wires and the steering wires 76, to pass therethrough. In an exemplary embodiment, the slider blocks 61 are arranged such that each passageway 96 is coaxial with the longitudinal axis 86.

Figure 6:
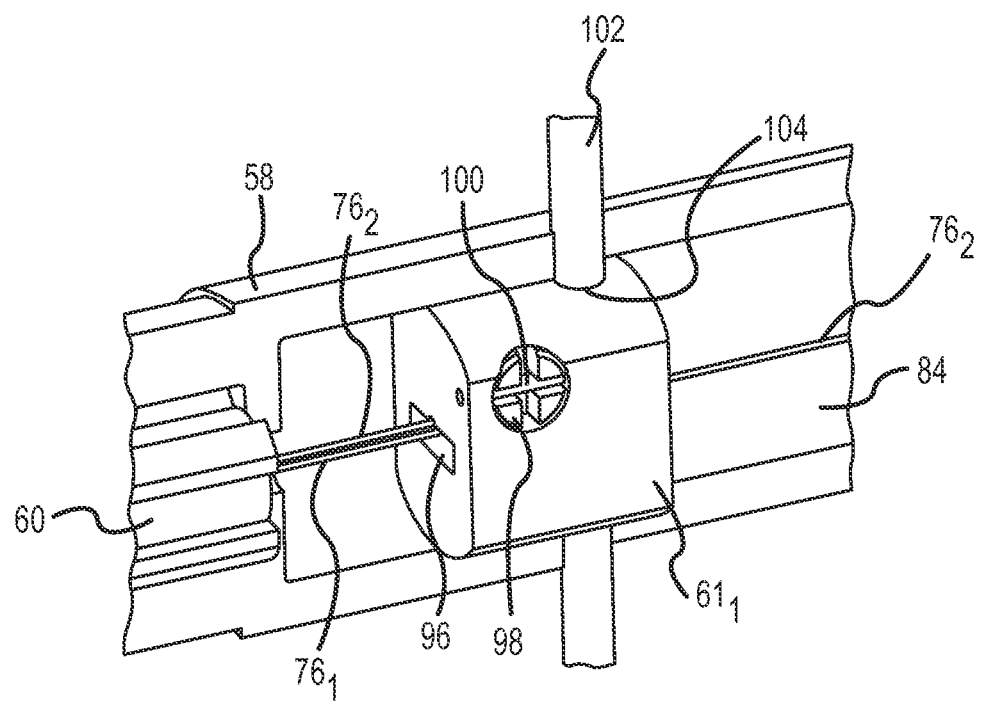
FIG. 6 is an enlarged isometric side view of a portion of the rotatable assembly illustrated in FIG. 5 showing, with particularity, a slider block of the rotatable assembly.

The steering wires 76 may be coupled with respective slider blocks 61 in a number of ways. For example, and with reference to FIG. 6, in one embodiment, a slider block 61 includes a locking screw 98 disposed therein. In such an embodiment, the steering wire 76 extends into the passageway 96 of the slider block 61 and is interested into, for example, a hole or slot in the locking screw 98, and is then wrapped around a portion of the screw 98. The steering wire 76 may be wrapped around the screw by rotating the exposed head of the screw 98, as is illustrated in FIG. 6. In such an embodiment, the slider block 61 may further include a pin 100 that extends through a portion of the body of the slider block 61 and into a groove in the head of the screw 98. The pin 100 prevents the screw 98 from rotating, and therefore, prevents the steering wire 76 from unraveling.

As illustrated in FIG. 5, in an exemplary embodiment, each slider block 61 further includes one or more dowel pins 102 outwardly extending therefrom in a radial direction relative to the longitudinal axis 86. In an exemplary embodiment, the slider block 61 has a bore 104 therein that is configured to receive the dowel pin 102. In an exemplary embodiment, the bore 104 is a closed bore such that the dowel pin 102 only extends from only one side of the slider block 61. In an another exemplary embodiment, such as that illustrated in FIG. 5, the bore 104 is a through-bore such that the dowel pin 102 extends all the way through the slider block 61 and protrudes radially outwardly therefrom on diametrically opposite sides of the slider block 61. While the description above has been with respect to a single dowel pin 102 and a single bore 104, in other exemplary embodiment, the slider block 61 may have multiple dowel pins 102 disposed in one or more bores 104 therein, and such embodiments remain within the spirit and scope of the present disclosure.

In any event, when the rotatable assembly 42 is assembled, each dowel pin 102 extends through, and is configured to travel within, one or more respective elongated slots 94 in the housing 58. The dowel pins 102 of each slider block 61 are configured to engage and be coupled with a respective drive interface 64 of the cartridge 36 to effect the movement of the slider blocks 61.

As will be described in further detail below, the distal portion of the medical device 44 can be deflected by selective tensioning of the steering wire(s) 76 thereof. To that end, each slider block 61 is configured to translate within the cavity 84 to cause a tension response in the steering wire 76 associated therewith. More particularly, and as more fully described in PCT/US2011/030764 entitled "Intuitive User Interface Control for Remote Catheter Navigation and 3D Mapping and Visualization Systems," published as WO/2011/123669, the entire disclosure of which is incorporated herein by reference, each slider block 61 can be translated in a proximal direction (i.e., away from the anchor member 60) to apply tension to the corresponding steering wire 76, thereby causing a corresponding deflection in a direction toward the steering wire 76. In an embodiment such as that described herein where there are two steering wires 76, and therefore, two slider blocks 61, as the slider block 61 associated with a first steering wire 76 translates in a first, proximal direction, the other slider block 61 reactively moves or retracts in a second, substantially opposing distal direction (i.e., toward the anchor member 60) to account for the tensioning of the first steering wire 76. By translating the slider blocks 61 along the longitudinal axis 86, the medical device 44 can be deflected or straightened as desired.

As briefly described above, in an exemplary embodiment, the rotatable assembly 42 further comprises an electrical port 66. As illustrated in FIGS. 4 and 5, the port 66 is disposed within the second end 82 of the housing 58, and within the opening 90 thereof, in particular. Accordingly, in such an embodiment, the opening 90 is sized and configured to receive and retain the electrical port 66. The electrical port 66 has a first end 106 and a second end 108. The first end 106 is disposed within the cavity 84 of the housing 58 and is configured to be electrically coupled to, for example, one or more lead wires of one or more sensors 74 of the medical device 44 that extend through the cavity 84. The second end 108 is disposed external to the housing 58 and comprises an electrical connector configured to be electrically coupled with a complementary electrical connector.

For example, the second end 108 of the port 66 may comprise a male plug connector having a plurality of pin contacts that is configured to be mated with a female receptacle connector having a plurality of socket contacts, or vice versa. As will be described below, in an exemplary embodiment, the electrical port 66, and the second end 108 thereof, in particular, is configured to be electrically coupled with an electrical connector of a commutator. Alternatively, the electrical port 66 may be electrically coupled with an electrical connector of a cable or bus that is, in turn, electrically connected to one or more other components of the RCGS 10. As illustrated in FIG. 2, for example, in an exemplary embodiment, the second end 82 of the rotatable assembly 42 is sized and shaped to be disposed within the flanged opening 56 of the outer housing 40. Accordingly, in such an embodiment, the electrical port 66 is disposed within and is accessible through the opening 56 in the housing 40.

As was briefly described above, in the embodiment illustrated in FIG. 4, the rotatable assembly 42 further comprises one or more drive interfaces 62. Each drive interface 62 is fixedly coupled with the housing 58 of the rotatable assembly 42 and is configured to be engaged with a drive system of the manipulation base 38 to impart rotational movement onto the rotatable assembly 42. In an embodiment wherein there are multiple drive interfaces 62, each drive interface 62 may be engaged with a respective drive system, or all of the drive interfaces 62 may be engaged with a common drive system. While the rotatable assembly 42 may comprise any number of drive interfaces 62, for purposes of illustration, the description below will be limited to an embodiment wherein the rotatable assembly 42 includes a single drive interface 62.

As illustrated in FIG. 4, in an exemplary embodiment, the drive interface 62 comprises a collar that is fixedly mounted on and surrounds or circumscribes the housing 58 of the rotatable assembly 42. In an exemplary embodiment, the drive interface 62 is mounted on the housing 58 at the first end 80 thereof, though the present disclosure is not meant to be so limited. As illustrated in FIG. 4, in an exemplary embodiment the drive interface 62 comprises a body 110 having a through-bore 112 disposed therein that has a diameter slightly larger than the outer diameter of at least a portion of the housing 58 to allow the drive interface 62 to be placed over and onto the housing 58. While the bore 112 is described and depicted herein as having a circular cross-section, it will be appreciated that the cross-sectional shape will depend on the cross-sectional shape of the housing 58. Accordingly, embodiments wherein the bore 112 has a cross-sectional shape other than circular remain within the spirit and scope of the present disclosure.

As will be described in greater detail below, in an exemplary embodiment, at least a portion of the body 110 has a circular cross-section thereby defining an annular surface 114. The annular surface 114 is configured to operatively engage a drive system of the manipulation base 38, which is configured to impart rotational movement onto the drive interface 62, and thus, the rotatable assembly 42, about the longitudinal axis 86. In an exemplary embodiment, the drive interface 62 comprises a gear, and therefore, the annular surface 114 has a plurality of teeth extending outwardly therefrom. In another exemplary embodiment, however, the annular surface 114 is smooth.

In an embodiment wherein the medical device 44 comprises one or more steering wires 76, and the rotatable assembly 42, therefore, comprises one or more slider blocks 61, the rotatable assembly 42 further comprises a respective drive interface 64 for each slider block 61. Accordingly, with continued reference to FIG. 4, in an exemplary embodiment wherein the rotatable assembly 42 comprises two slider blocks 61, the rotatable assembly 42 also comprises two drive interfaces 64 (drive interfaces $64_1$, $64_2$). Each drive interface 64 is coupled with a respective slider block 61 and is configured to be engaged with a corresponding drive system of the manipulation base 38 to impart translational movement onto the respective slider block 61.

As illustrated in FIG. 4, in an exemplary embodiment, each drive interface 64 comprises a collar that surrounds or circumscribes the housing 58 of the rotatable assembly 42. In such an embodiment, each drive interface 64 comprises a body 116 defining a longitudinal axis 118, and has an axially-extending through-bore 120 disposed therein. As illustrated in FIG. 4, the axis 118 is coaxial with the axis 86 of the housing 58. The bore 120 has a diameter that is slightly larger than the outer diameter of at least a portion of the housing 58 to allow the drive interface 64 to be placed over and onto the housing 58. While the bore 120 is described and depicted herein as having a circular cross-section, it will be appreciated that the cross-sectional shape will depend on the cross-sectional shape of the housing 58. Accordingly, embodiments wherein the bore 120 has a cross-sectional shape other than circular remain within the spirit and scope of the present disclosure.

As illustrated in FIG. 4, the body 116 of each drive interface 64 further comprises one or more channels 122 therein, each configured to receive one or more dowel pins 102 of the corresponding slider block 61. More particularly, each channel 122 extends within or through the body 116 in a radial direction relative to the longitudinal axis 118 thereof. In an exemplary embodiment, the channels 122 extend through the body 116 (i.e., extend from the surface of the bore 120 through the outer surface of the body 116) and when the drive interface 64 is mounted on the housing 58 and is properly aligned with the slider block 61, is configured to allow for the dowel pin 102 to be inserted through the channel 122, through the slot 94 in the housing 58, and into the bore 104 in the slider block 61. In such an embodiment, the dowel pin 102 may be further inserted into a second channel 122 diametrically opposing the first channel 122 such that the dowel pin 102 would extend through a first channel 122, a first slot 94 in the housing 58, the port 104 in the slider block 61, a second slot 94 in the housing 58, and a second channel 122.

While the description above is primarily with respect to the channels 122 extending from the surface of the bore 120 through the outer surface of the body 116, in other embodiments, some or all of the channels 122 may not extend all the way through the body 116, but rather may extend from the surface of the bore 120 to a point in the body 116 short of the outer surface thereof. For instance, in an exemplary embodiment, the body 116 has a first channel 122 that extends from the surface of the bore 120 through the outer surface of the body 116, and a second channel 122 that is disposed directly across the bore 120 from the first channel 122 (i.e., diametrically opposed) and that extends from the surface of the bore 120 to a point short of the outer surface of the body 116. In such an embodiment, a dowel pin 102 may be inserted through the first channel 122, through a slot 94 in the housing 58, through the bore 104 in the slider block 161, and then into the second channel 122 such that the pin 102 extends within, but not through, the body 116 relative to the second channel 122.

As illustrated in FIG. 4, in an exemplary embodiment, the body 116 further comprises a flange 124 at one axial end thereof extending outwardly therefrom in a radial direction relative to the longitudinal axis 118. In such an embodiment, the channels 122 may be disposed within the flange 124. As will be described in greater detail below, in an exemplary embodiment, the flange 124 is configured to operatively engage a drive system of the manipulation base 38, which, as was briefly described above, is configured to impart translational movement onto the drive interface 64, thereby causing translational movement of the corresponding slider block 61. The body 116 of the drive interface 64 may be of a unitary construction, or alternatively, may be formed of a plurality of pieces that may be detachably joined together. In either instance, the body 116 may be formed of plastic, though the present disclosure is not meant to be so limited.

As briefly described above, at least a portion of the cartridge housing 40 comprises a base plate (base plate 48). In an exemplary embodiment such as that illustrated in FIG. 4, the base plate 48 includes one or more recesses or indented portions 126. These recesses 126 are located such that when the rotatable assembly 42 is disposed within the housing 40, the recesses 126 are proximate the drive interfaces 64. The recesses 126 are sized and shaped to allow the drive interfaces 64 to freely rotate as the rotatable assembly 42 rotates, and to move axially as the pin 102 corresponding thereto travels within the slot 94 in the housing 58, without contacting the base plate 48. As also illustrated in FIG. 4, the base plate 48 may also include a plurality of apertures 128 (e.g., 128₁-128₅) therein that, as will be described more fully below, are configured to permit the operative engagement of the drive interfaces 62, 64 with the respective drive systems of the manipulation base 38. In an exemplary embodiment, each of the apertures 128 comprises an elongated slot (slot 128) that either extends axially or radially relative to the longitudinal axis 86 of the housing 58 of the rotatable assembly 42. For example, in the particular embodiment described in detail herein, the base plate 48 comprises four axially extending slots 128 (slots 128₁-128₄), and one radially extending slot 128 (slot 128₅).

In an exemplary embodiment, the base plate 48 further comprises one or more sockets or recesses 130 configured to allow the cartridge 36 to be removably attached to the manipulation base 38. More particularly, in an exemplary embodiment, one or more recesses or sockets 130 are configured to receive and retain complementary locking pins or latch mechanisms, for example, of a mounting plate of the manipulation base 38. The recesses or sockets 130 may include an interference lock such as a spring detect or other locking means. Alternatively, in another exemplary embodiment, the base plate 48 comprises one or more locking pins or latch mechanisms that are configured to be mated with sockets or recesses disposed in the mounting plate of the manipulation base 38.

As illustrated in FIG. 4, in an exemplary embodiment, the base plate 48 may further include a memory or storage device 131, such as, for example and without limitation, an electrically erasable programmable read-only memory (EEPROM) or an radio-frequency identification (RFID) chip. The memory 131 may contain, for example, identifying information relating to the cartridge 36 and/or the various components thereof. The information may comprise for example, the make, model, serial number, physical dimensions, special features, and/or calibration data related to the medical device 44 or the rotatable assembly 42. One exemplary purpose of providing this information relates to the instance wherein the use of a cartridge 36 and associated rotatable assembly 42 or medical device 44 thereof is restricted to a single use. Accordingly, the information contained in the memory 131 may be provided to allow the RCGS 10 to determine, for example, whether a particular device associated with the memory 131 has been previously used, and if so, to provide an indication to the user to remove that particular device or cartridge 36 from the manipulation base 38.

Figure 7:
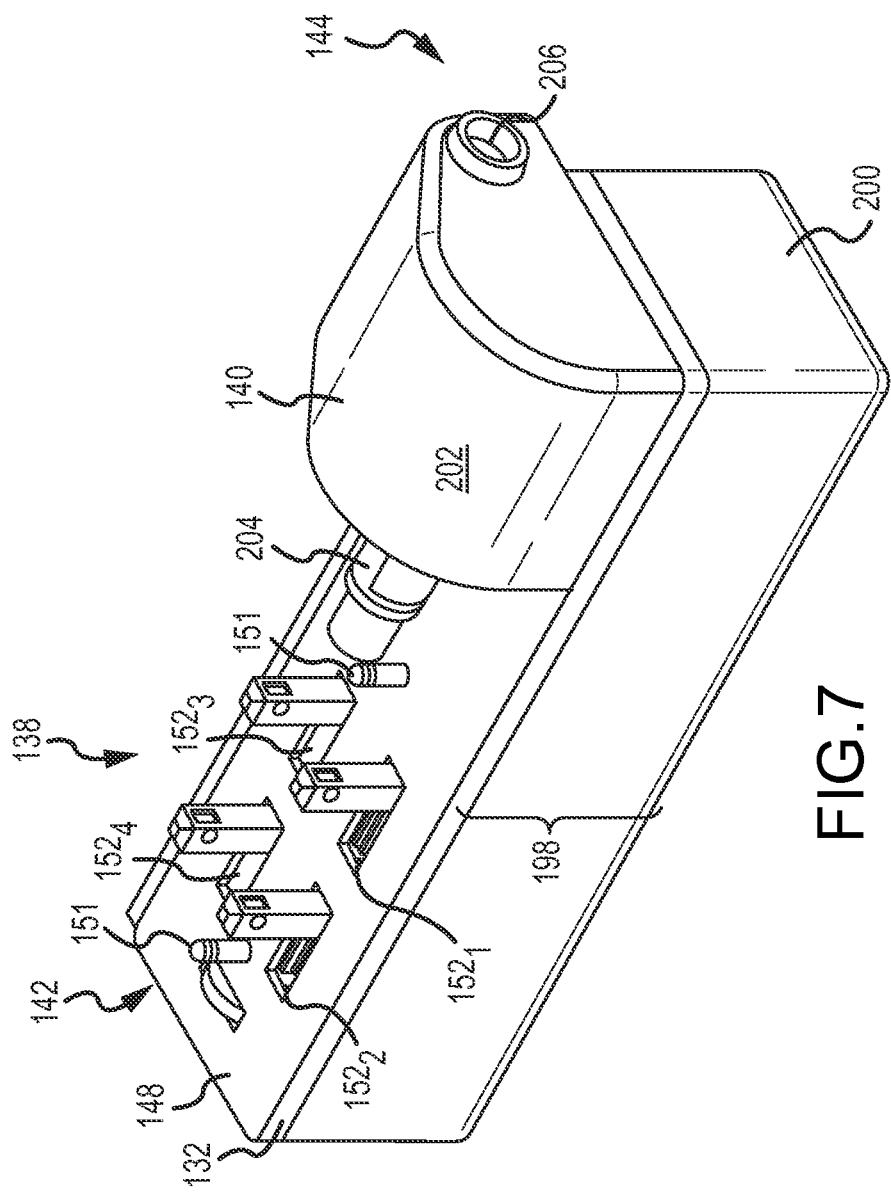
FIG. 7 is an isometric view of an exemplary manipulation base of the drive assembly illustrated in FIG. 2.
Figure 8:
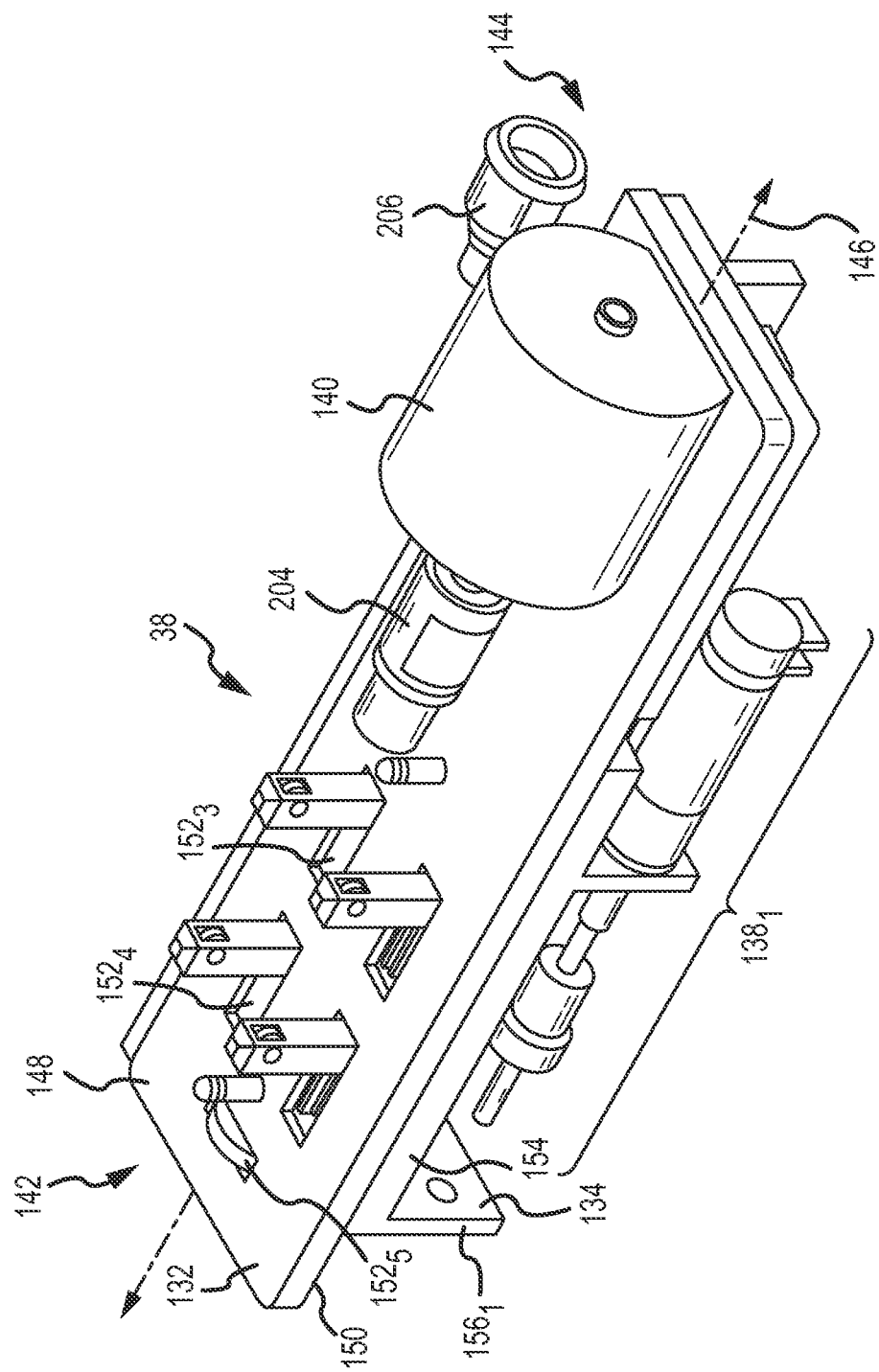
FIG. 8 is an isometric view of the exemplary manipulation base illustrated in FIG. 7, wherein a portion of the housing thereof, and the housing of a commutator mounted thereon, have been removed to show the exemplary manipulation base in greater detail.

With reference to FIGS. 7-13, the manipulation base 38 will now be described. In an exemplary embodiment and in general terms, the manipulation base 38 comprises a mounting plate 132, a support frame 134 (best shown in FIG. 9) mounted onto the mounting plate 132, and a high-precision drive system 136 (best shown in FIGS. 9 and 10) that is supported by the support frame 134 and configured to operatively engage and impart rotational movement onto the drive interface 62 of the cartridge 36. In an exemplary embodiment, the manipulation base 38 further comprises one or more high-precision drive systems 138 (best shown in FIGS. 9 and 10) also supported by the support frame 134 and configured to operatively engage and impart translational movement onto respective drive interfaces 64 of the cartridge 36. As described above, in an exemplary embodiment the cartridge 36, and the rotatable assembly 42 thereof, in particular, comprises two drive interfaces 64, and therefore, in such an embodiment the manipulation base 38 includes two drive systems 138 (drive systems 138₁, 138₂), one for each drive interface 64. As illustrated in FIGS. 7 and 8 and as will be described in greater detail below, in an exemplary embodiment, the manipulation base 38 may also still further comprise a commutator 140.

With particular reference to FIGS. 7 and 8, the mounting plate 132 has a first end 142, a second end 144, and a longitudinal axis 146 extending therebetween. The mounting plate 132 further comprises a first side 148 and a second side 150. The first side 148 is configured to have the cartridge 36 removably attached thereto. Accordingly, when the cartridge 36 is attached to the manipulation base 38, the first side 148 of the mounting plate 132 faces the cartridge base plate 48, while the second side 150 faces away from the cartridge 36. In an exemplary embodiment, the first side 148 comprises one or more locking pins or latching mechanisms 151 extending radially outwardly therefrom relative to the longitudinal axis 146 that are configured to be mated with complementary recess or sockets 130 of the cartridge base plate 48. Alternatively, in an other exemplary embodiment, the first side 148 of the mounting plate 132 may having one or more recesses or sockets (not shown) disposed therein that are configured to receive and retain one or more complementary locking pins or latch mechanisms of the cartridge base plate 48. In such an embodiment, the recesses or sockets may include an interference lock such as a spring detect or other locking means.

With continued reference to FIGS. 7 and 8, the mounting plate 132 further comprises a plurality of apertures 152 therein (e.g., $152_1$-$152_5$). In an exemplary embodiment, each of the apertures 152 comprises an elongated slot (slot 152) that either extends axially or radially relative to the axis 146 of the mounting plate 132. For example, in the particular embodiment described in detail herein, the mounting plate 132 comprises four axially extending slots 152 (slots $152_1$-$152_4$), and one radially extending slot 152 (slot $152_5$). For reasons that will be apparent below, the arrangement of the slots 152 in the mounting plate 132 may mirror that of the slots 128 in the cartridge base plate 48 (i.e., the slots 152 of the mounting plate 132 will be aligned with corresponding slots 128 of the base plate 48 when the base plate 48 and mounting plate 58 are arranged together). In an exemplary embodiment, the mounting plate 132 is formed of plastic, though the present disclosure is not meant to be so limited.

Figure 9:
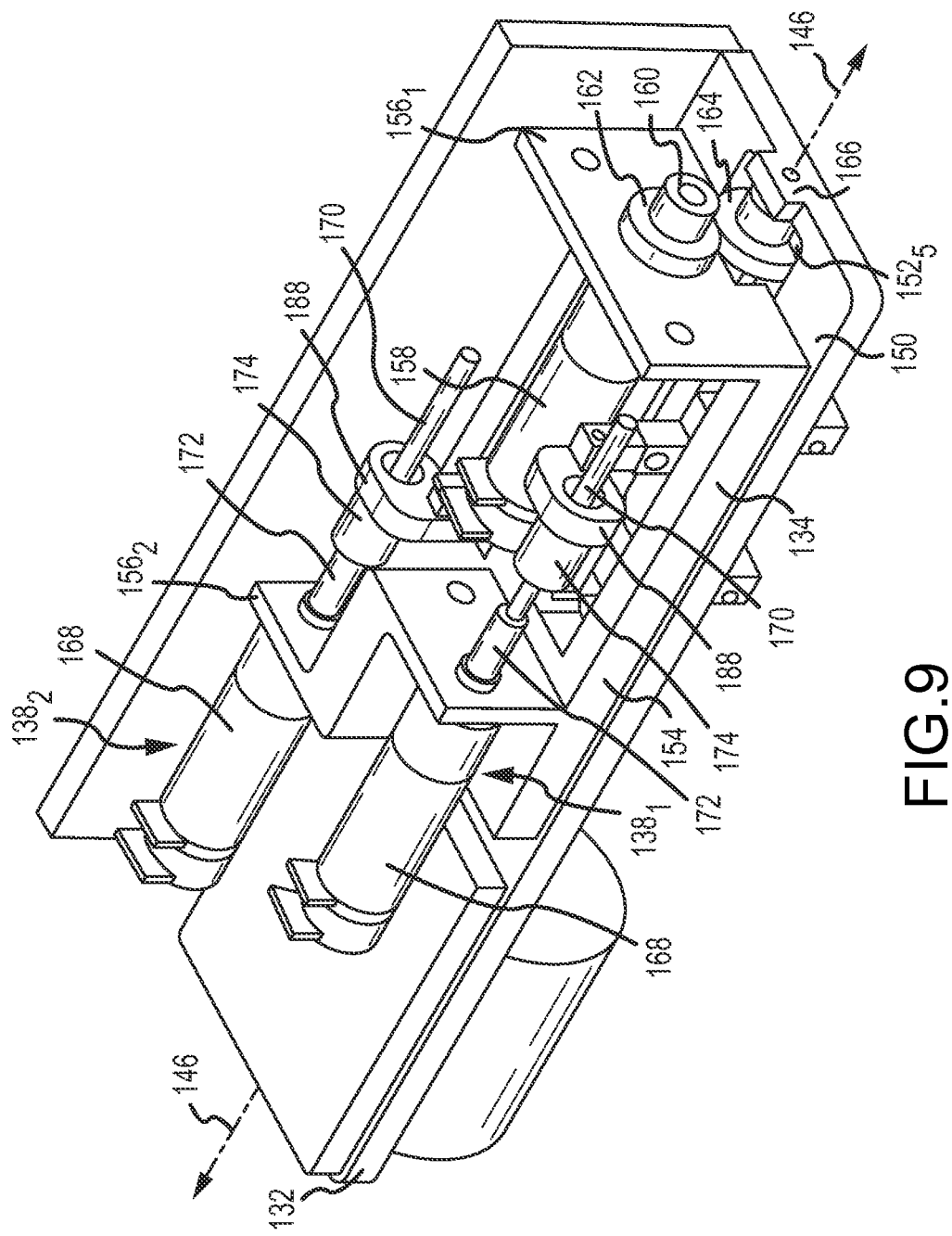
FIG. 9 is an isometric view of the exemplary manipulation base illustrated in FIG. 8 showing the underside or bottom of the manipulation base.

As illustrated in FIGS. 8 and 9, the second side 150 of the mounting plate 132 is configured to have the support frame 134 mounted thereto. The support frame 134 comprises a horizontal portion 154 (i.e., extending axially relative to the axis 146) and one or more vertical portions 156 (i.e., extending radially relative to the axis 146). In the embodiment being described in detail herein, the support frame 134 comprises two vertical portions 156 (vertical portions $156_1$, $156_2$). As illustrated in FIG. 9, one side of the horizontal portion 154 is planar, and the other has the vertical portions 156 extending outwardly therefrom. The planar side of the horizontal portion 154 is configured to be affixed or mounted to the second side 150 of the mounting plate 132, while each of the vertical portions 156 are configured to support one or more of the drive systems 136, 138 of the manipulation base 38, and the output shafts of the motors thereof, in particular.

The support frame 134 may be mounted to the mounting plate 132 in a number of ways. For example, conventional fasteners may be used to affix the support frame 134 to the mounting plate 132. Alternatively, an adhesive may be used, or the frame 134 may be removably or detachably coupled to the mounting plate using any number of techniques known in the art, including, for example and without limitation, those described elsewhere herein. Further, the support frame 134 may be formed of plastic, though the present disclosure is not meant to be so limited.

As briefly described above and with reference to FIGS. 9 and 10, the manipulation base 38 comprises at least one drive system 136. In an exemplary embodiment, the drive system 136 comprises a rotary actuator configured to operatively engage and impart rotational movement onto the drive interface 62 of the cartridge 36. In such an embodiment, the rotary actuator may comprise an electric rotary motor 158 having an output shaft 160. In an embodiment, the axis of rotation of the output shaft 160 is parallel to, and, in an exemplary embodiment, vertically aligned with, the longitudinal axis 146 of the mounting plate 132. In an exemplary embodiment, the drive system 136 is mounted to the second side 150 of the mounting plate 132 by the support frame 134. More particularly, the vertical portion $156_1$ of the support frame 134 comprises an aperture therein that is configured to receive the output shaft 160 of the motor 158. The support frame 134 is configured to support the motor 158 and to ensure that it is properly oriented with respect to other components of the drive system 136.

Figure 10:
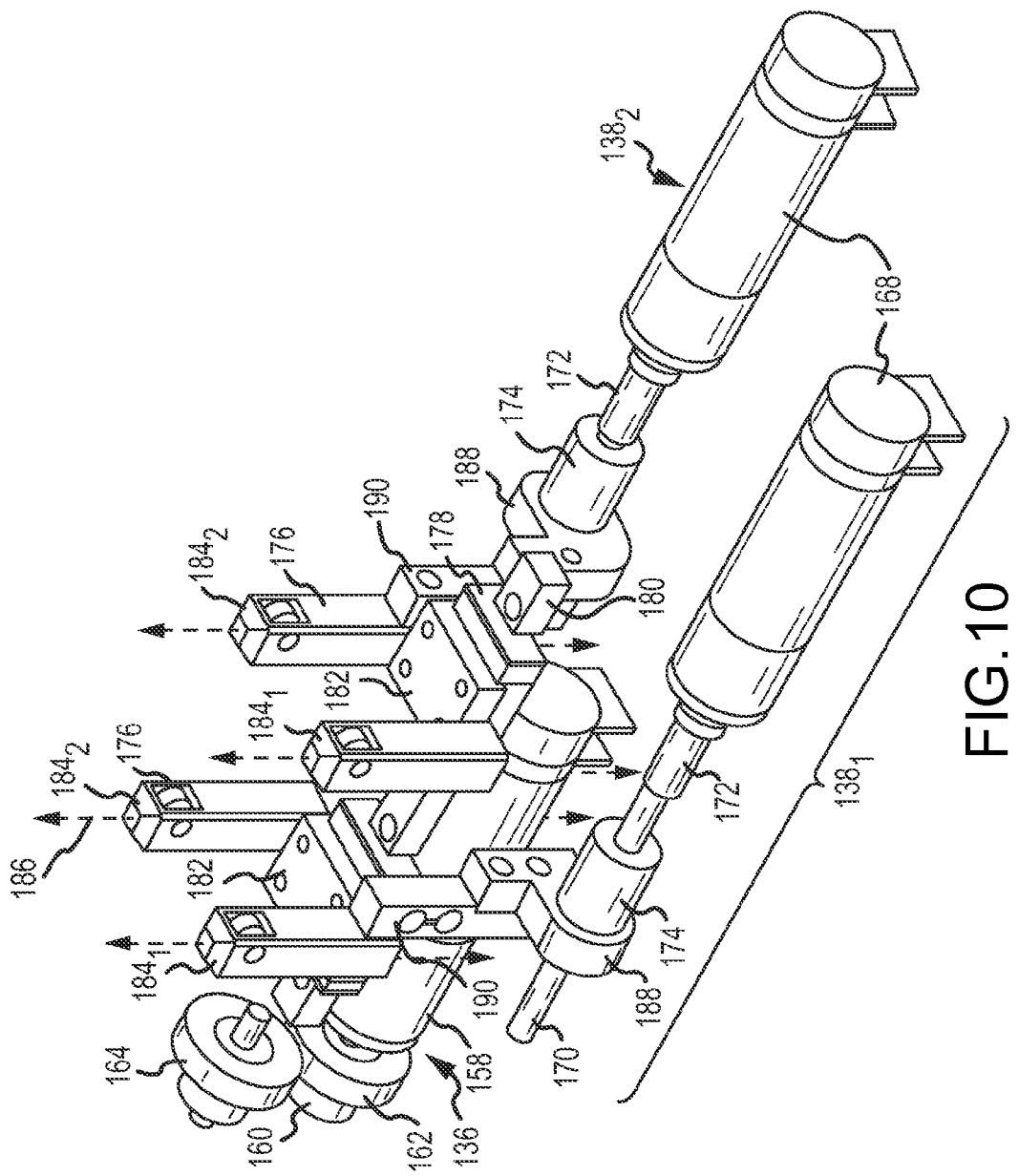
FIG. 10 is an isometric view of the exemplary manipulation base illustrated in FIGS. 7 and 8, wherein the mounting plate and support frame thereof have been removed to show the manipulation base in greater detail.

As best shown in FIG. 10, the drive system 136 further comprises a rotatable member 162 coaxially arranged with, and mounted on, the output shaft 160. In an exemplary embodiment, the rotatable member 162 comprises an external gear. In another exemplary embodiment, the rotatable member 162 comprises a wheel having a smooth annular surface (i.e., no teeth). The particular configuration of the rotatable member 162 will depend, at least in part, on the configuration of the drive interface 62 of the cartridge 36 (e.g., whether the drive interface 62 comprises a gear or has a smooth annular surface 114). In any event, in an exemplary embodiment, the rotatable member 162 is configured to operatively engage the drive interface 62 and to impart the rotational motion generated by the motor 158 onto the drive interface 62, and therefore, the rotatable assembly 42 of the cartridge 36. More particularly, in an exemplary embodiment, the rotatable member 162 is aligned with and partially extends through, the slot $152_5$ in the mounting plate 132. The rotatable member 162 extends far enough through the slot $152_5$ that when the cartridge 36 is attached to the mounting plate 132, a portion of the rotatable member 156 also extends through the slot $128_5$ in the cartridge base plate 48. The rotatable member 162 extends far enough through the slot $128_5$ that it operatively engages the annular surface 114 of the drive interface 62. Accordingly, in an embodiment wherein the annular surface 114 and the annular surface of the rotatable member 162 are each smooth, the operative engagement between the drive interface 62 and the rotatable member 162 comprises a friction interface, while in an embodiment wherein the drive interface 62 and the rotatable member 162 each comprise gears, the operative engagement comprises a gear arrangement.

In another exemplary embodiment, rather than the rotatable member 162 directly engaging the drive interface 62, a second rotatable member 164 is disposed between and operatively engages both the drive interface 62 and the first rotatable member 162. Thus, in such an embodiment, the second rotatable member 164 is configured to impart the rotational motion generated by the motor 158 onto the drive interface 62, and therefore, the rotatable assembly 42. As with the first rotatable member 162, in an exemplary embodiment, the second rotatable member 164 comprises an external gear. In another exemplary embodiment, the second rotatable member 164 comprises a wheel having a smooth annular surface (i.e., no teeth). The particular configuration of the second rotatable member 164 will depend, at least in part, on the configuration of both the rotatable member 162 and the drive interface 62 of the cartridge 36 (e.g., whether the rotatable member 162 and the drive interface 62 comprise gears or have smooth annular surfaces).

In exemplary embodiment, the second rotatable member 164 is mounted to the mounting plate 132 in such a manner that it is operatively engaged with the first rotatable member 162, and its axis of rotation is parallel to and vertically aligned that of the output shaft 160. More particularly, in an exemplary embodiment such as that illustrated in FIG. 9, the mounting plate 132 has a pair of axially spaced mounting tabs 166 that extend radially outwardly (e.g., downward) from the second surface 150 relative to the longitudinal axis 146 of the mounting plate 132. In an exemplary embodiment, the tabs 166 are disposed on diametrically opposite sides of the slot $152_5$ such that when the second rotating member 164 is mounted to the mounting tabs 166, at least a portion of the rotatable member 164 is disposed within, and extends through, the slot $152_5$. The second rotatable member 164 extends far enough through the slot $152_5$ that when the cartridge 36 is attached to the mounting plate 132, a portion of the second rotatable member 164 also extends through the slot $128_5$ in the cartridge base plate 48. The second rotatable member 164 also extends far enough through the slot $128_5$ that it operatively engages the annular surface 114 of the drive interface 62. Accordingly, in an embodiment wherein the annular surface 114 and the annular surfaces of the rotatable members 162, 164 are each smooth, the operative engagement therebetween comprises a friction interface, while in an embodiment wherein the drive interface 62 and the rotatable members 162, 164 each comprise gears, the operative engagement comprises a gear arrangement.

Whether the rotatable member 162 or the second rotatable member 164 engages the drive interface 62, the drive system 136 is configured to impart rotational movement onto the drive interface 62, and thus, the rotatable assembly 42. Accordingly, if rotation in a first direction is desired, the drive system 136 is configured to cause the motor 158 to rotate the output shaft 160 thereof in the appropriate direction to achieve the desired rotation. As will be described in greater detail below, the drive system 136, and the motor 158 thereof in particular, is electrically coupled to, and configured to be controlled by, one or more motor controllers in the manner described below.

While the description above has been primarily with respect to an embodiment wherein the drive system 136 is disposed below or underneath the drive interface 62 when the cartridge 36 and manipulation base 38 are assembled together, the present invention is not meant to be so limited. For example, in another exemplary embodiment, the drive system 136 may be axially arranged with the drive interface 62 with respect to the longitudinal axis 86 of the rotatable medical device assembly housing 58 (i.e., the drive system 136 may be disposed in front of or behind the rotatable medical device assembly 42). Accordingly, in such an embodiment, the motor 158 of the rotary actuator of the drive system 136 may mounted on the first side 148 of the mounting plate 132 and have a an output shaft 160 that is configured to operatively engage the drive interface 62 and to impart rotational movement onto the rotatable medical device assembly 42. For example, in an exemplary embodiment, the shaft (shaft 204, as will be described below) of the commutator 140 may be operatively engaged with the drive interface 62 and be configured to be driven by the motor 158 of the drive system 136 to impart rotational movement onto the drive interface 62, and therefore, the rotatable medical device assembly 42. Alternatively, the drive interface 62 may be operatively engaged with, and driven directly by, the output shaft 160 of the motor 158.

As briefly described above, and with continued reference to FIGS. 9 and 10, in an exemplary embodiment, the manipulation base 38 further comprises one or more drive systems 138 configured to impart translational movement onto respective drive interfaces 64 of the cartridge 36. As described above, in an exemplary embodiment, the cartridge 36, and the rotatable assembly 42 thereof, in particular, comprises two drive interfaces 64, and therefore, in such an embodiment the manipulation base 38 includes two drive systems 138 (drive systems $138_1$, $138_2$)—one for each drive interface 64.

With particular reference to FIG. 10, in an exemplary embodiment, each of the drive systems 138 comprises an electromechanical device that is configured to operatively engage and impart translational movement onto a respective drive interface 64. More specifically, the drive system may comprise an electric motor 168 and a motor-driven ball screw. The ball screw comprises a screw portion 170 coupled to the output shaft of the motor 168 by a coupler 172, and a ball nut 174 that is configured to travel along the screw 170 as it is rotated by the motor 168. In an exemplary embodiment, each of the ball nuts 174 are configured to travel in an axial direction relative to the longitudinal axis 146 of the mounting plate 132. While the description below will be limited to an embodiment wherein the drive system 138 comprises a motor-driven ball screw, it will be appreciated that the present disclosure is not meant to be so limited. Rather, in other exemplary embodiments, the drive system 138 may comprise devices or components other than a ball screw, such as, for example, a motor-driven lead screw, a linear motor, a stepper motor drive configured to drive a belt, and other like devices, and such embodiments remain within the spirit and scope of the present disclosure.

As with the drive system 136 described above, in an exemplary embodiment, each drive system 138 is mounted onto the second side 150 of the mounting plate 132 by the support frame 134. More particularly, and with reference to FIG. 9, the vertical portion $156_2$ of the support frame 134 comprises a pair of apertures therein that are configured to receive the output shafts of the motors 168 (or the coupler 172 that couples the output shaft to the screw 170). The support frame 134 is configured to support the motors 168 and to ensure that each one is properly oriented or aligned with respect to the other components of the respective drive system 138.

Each of the drive systems 138 further comprises a driven member 176 configured to be driven by the respective motor 168 and ball screw combination. With reference to FIG. 10, in an exemplary embodiment, the driven member 176 is integral with, or fixedly coupled to (e.g., using conventional fasteners) a bearing block 178, which, in turn, is moveably coupled to a corresponding bearing rail 180. In the illustrated embodiment, the bearing rail 180 is mounted on the second side 150 of the mounting plate 132. Accordingly, as the driven member 176 is driven by the motor 168 and ball screw of the corresponding drive system 138, the driven member 176 and the bearing block 178 travel along the bearing rail 180.

In an exemplary embodiment, the bearing blocks 178 corresponding to the respective driven members 176 are coupled to the same bearing rail 180. In another exemplary embodiment, however, each bearing block 178 may be coupled to a respective bearing rail 180. In either instance, the bearing rail 180 may take the form of a track upon which a bearing block 178 may be mounted and along which it may travel. In the embodiment described in detail herein, each of the bearing blocks 178 are mounted on a common bearing rail 180, and the bearing rail 180 has a longitudinal axis that is parallel to the longitudinal axis 146 of the mounting plate 132. Further, in an exemplary embodiment, each of the driven members 176, the bearing blocks 178, and the bearing rail 180 are formed of plastic, though the present disclosure is not intended to be so limited.

As illustrated in FIGS. 7-10, in an exemplary embodiment, each of the driven members 176 comprises a drive fork. While the description below will be primarily with respect to such an embodiment, it will be appreciated that the present disclosure is not meant to be limited to such an embodiment, but rather embodiments wherein the driven member 176 is other than a drive fork remain within the spirit and scope of the present disclosure. Accordingly, as illustrated in FIG. 10, each of the driven members 176 comprises a base 182 and a pair of prongs 184 extending outwardly from the base 182. Each prong 184 defines a respective longitudinal axis 186 that is perpendicular to the axis 146 of the mounting plate 132, and that is also disposed in a plane that is perpendicular to the plane in which the axis 146 is disposed.

Figure 11:
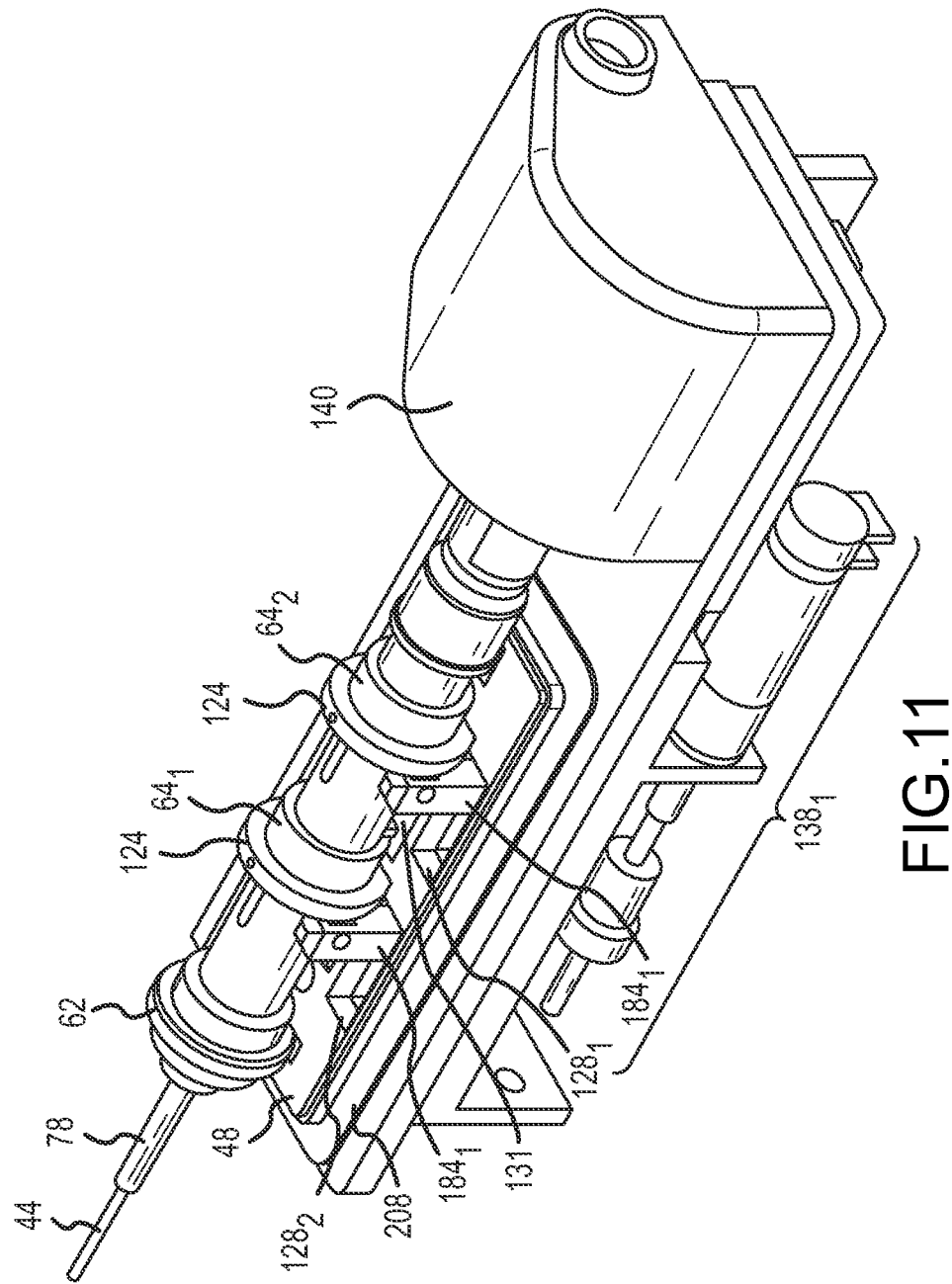
FIG. 11 is an isometric view of the exemplary drive assembly illustrated in FIG. 2, wherein portions of the housings of the cartridge and manipulation base thereof have been removed to show the exemplary drive assembly in greater detail.

In an exemplary embodiment, the base 182 is coupled to or integral with the bearing block 178 described above. Further, each of the prongs 184 extend axially relative to the longitudinal axis 186 thereof from the base 182, and through a corresponding slot 152 in the mounting plate 132. More particularly, the first prong $184_1$ of the driven member 176 corresponding to the drive system $138_1$ extends through the slot $152_2$ and is configured to travel therein in an axial direction relative to the axis 146 of the mounting plate 132. Similarly, the second prong $184_2$ extends through the slot $152_4$ that is next to the slot $152_2$, and is configured to travel therein in an axial direction relative to the axis 146. As illustrated in FIG. 11, each of the prongs $184_1$, $184_2$ of the driven member 176 of the drive system $138_1$ extend far enough through the slots $152_2$, $152_4$ that when the cartridge 36 is attached to the manipulation base 38, the prongs $184_1$, $184_2$ also extend through the corresponding slots 128 in the cartridge base plate 48. The prongs $184_1$, $184_2$ extend far enough through the slots respective slots 128 in the base plate 48 that they operatively engage the flange 124 of the drive interface $64_1$.

As with the driven member 176 of the drive system $138_1$, the first prong $184_1$ of the driven member 176 corresponding to the drive system $138_2$ extends through the slot $152_1$ and is configured to travel therein in an axial direction relative to the axis 146 of the mounting plate 132. Similarly, the second prong $184_2$ extends through the slot $152_3$ that is next to the slot $152_1$, and is configured to travel therein in an axial direction relative to the axis 146. As illustrated in FIG. 11, each of the prongs $184_1$, $184_2$ of the driven member 176 corresponding to the drive system $138_2$ extend far enough through the slots $152_1$, $152_3$ that when the cartridge 36 is attached to the manipulation base 38, the prongs $184_1$, $184_2$ also extend through the corresponding slots 128 in the cartridge base plate 48. The prongs $184_1$, $184_2$ extend far enough through the respective slots 128 that they operatively engage the flange 124 of the drive interface $64_2$.

As illustrated in FIG. 10, each driven member 176 is coupled to a respective ball nut 174. In an exemplary embodiment, the driven member 176 and the ball nut 174 may be directly coupled together. In another exemplary embodiment, such as that illustrated in FIG. 10, for example, the driven member 176 is indirectly coupled to the ball nut 174. More particularly, the ball nut 174 may have a coupling 188 attached thereto. In an exemplary embodiment, the ball nut 174 is coupled with the coupling 188 using conventional fasteners. The coupling 188, in turn, and for reasons that will be described below, may be attached to a force sensor 190, such as, for example and without limitation, a strain gauge (strain gauge 190). The strain gauge 190 is then coupled with the driven member 176. In an exemplary embodiment, the strain gauge 190 is coupled with both the driven member 176 and the coupling 188 using conventional fasteners. Accordingly, as the ball nut 174 travels along the screw 170, the corresponding driven member 176 travels along the bearing rail 180 in the same direction the ball nut 174 travels. Alternatively, in another exemplary embodiment wherein the drive system 138 does not include a force sensor 190 such as that described above, the driven member 176 may be directly coupled to the coupling member 188.

With reference to FIG. 11, because the respective driven members 176 of the drive systems $138_1$, $138_2$ (and the prongs 184 thereof, in particular) are operatively engaged with respective drive interfaces 64 of the cartridge 36, translational movement may be imparted onto a particular drive interface 64 by translating the driven member 176 engaged with that drive interface 64. Thus, translating a driven member 176 results in the translation of the corresponding drive interface 64, and therefore, the slider block 61 coupled thereto, thereby resulting in the manipulation of the steering wire 76 associated with the slider block 61. Accordingly, if deflection of the medical device 44 in a given direction is desired, the drive system 138 operatively engaged with the drive interface 64 coupled to the slider block 61 corresponding to the appropriate steering wire 76 causes the driven member 176 thereof to translate in the direction that will result in the tensioning of the steering wire 76, thereby resulting in the deflection of the medical device 44. On the other hand, if deflection of the medical device in a different direction from that associated with a given steering wire 76, the drive system 138 may be further configured to cause the driven member 176 corresponding to that steering wire 76 to translate in a direction that will reduce the tensioning of the steering wire 76 so as to not impede the deflection of the medical device.

For example, and with reference to FIG. 11, in the instance wherein the steering wire $76_1$ corresponding to the slider block $61_1$ is to be tensioned, the drive system $138_1$ causes the ball nut 174 thereof to translate in a proximal direction (i.e., away from the anchor member 60 or distal end of the medical device 44). As a result, the driven member 176 corresponding thereto translates in the proximal direction, thereby applying a force onto the drive interface $64_1$ (i.e., the flange 124 thereof, or the surface of the interface $64_1$ facing the driven member 176) resulting in the translation of the slider block $61_1$ in a distal direction, and therefore, the tensioning of the steering wire $76_1$. To account for the tensioning of the steering wire $76_1$, the drive system $138_2$ may cause the ball nut 174 thereof to translate in a distal direction (i.e., toward the anchor member 60 or distal end of the medical device 44). As a result, the driven member 176 corresponding thereto translates in the distal direction, thereby allowing the slider block $61_2$ to also translate in the distal direction so as to not impede the tensioning of the steering wire $76_1$. Accordingly, each of the drive systems 138 is configured allow or to impart translational movement onto a respective drive interface 64, and thus, the slider block 61 coupled thereto. As will be described in greater detail below, each drive system 138, and the motors 168 thereof in particular, are electrically coupled to, and configured to be controlled by, one or more motor controllers in the manner described below.

Figure 12:
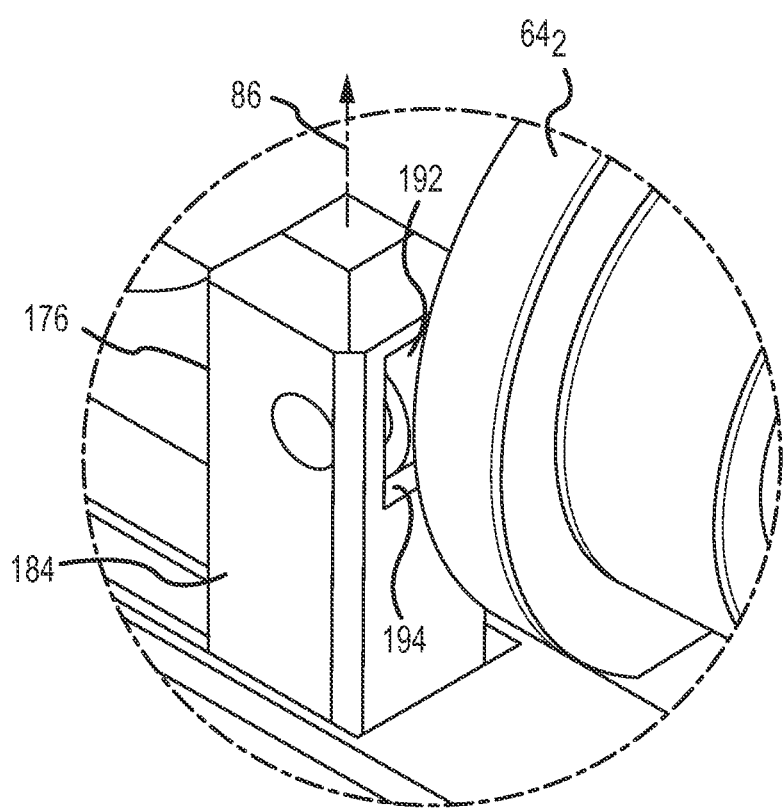
FIG. 12 is an enlarged isometric view of a portion of the exemplary drive assembly illustrated in FIG. 11 showing the operative engagement between a driven member of the manipulation base of the drive assembly, and a drive interface of the cartridge of the drive assembly in greater detail.
Figure 13:
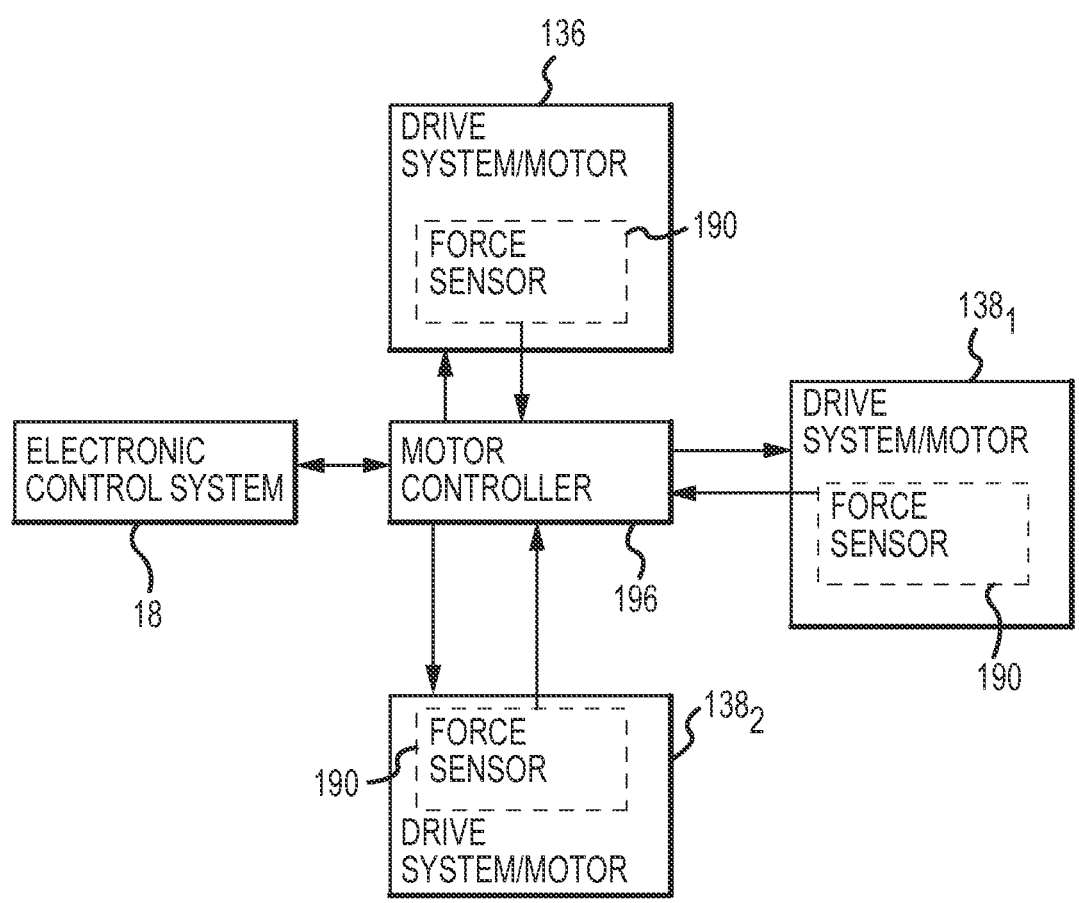
FIG. 13 is a diagrammatic and schematic view of electrical connections between components of the drive assembly illustrated in FIG. 2 and other components of the robotic control and guidance system of which the drive assembly is a part.

In addition to the above, in an exemplary embodiment such as that described herein, the driven members 176, and the prongs 184 thereof, in particular, may each comprise one or more rollers 192 configured to facilitate the rotation of the rotatable assembly 42 (i.e., to reduce the friction between the driven member 176 and the drive interface 64). More particularly, in an exemplary embodiment, each prong 184 of each driven member 176 comprises a roller 192. Accordingly, the body of each prong 184 has a recess 194 therein within which a roller 192 is mounted. As illustrated in FIG. 12, for example, the roller 192 partially protrudes from the recess 194 to such a degree that it contacts the surface of the corresponding drive interface 64. As a result, the drive interface 64 is allowed to roll along the roller 192 as the rotatable assembly 42 rotates. The rollers 192 may be formed of plastic or rubber, though the present disclosure is not intended to be so limited. While in the embodiment described and depicted herein each prong 184 of each driven member 176 includes a single roller 192, it will be appreciated that in other exemplary embodiments, either none or less than all of the prongs 184 may have rollers 192, or one or more prongs 184 may have more than one roller 192.

As briefly mentioned above, and as illustrated in FIG. 13, in an exemplary embodiment each of the drive systems 136, 138 are electrically coupled to, and configured to be controlled by, one or more motor controllers 196. In an exemplary embodiment, the manipulation base 38 includes a dedicated motor controller 196 for each drive system 136, 138, or for groups of drive systems (e.g., one for the drive system 136 and another for the drive systems 138). In another exemplary embodiment such as that described herein, the manipulation base 38 comprises a single motor controller 196 configured to control all of the drive systems 136,138 of the manipulation base 38. In an exemplary embodiment, the motor controller 196 includes a bus interface to facilitate exchange of information between the drive systems 136, 138 and, for example, the electronic control system 18 via a bus. In an embodiment, either the same bus interface, or one or more additional bus interfaces associated with the manipulation base 38 or the individual drive systems 136, 138 thereof, may be configured to provide operating power to the motors of the drive systems 136, 138. Alternatively, the manipulation base 38 may have a bus interface that is electrically coupled to the motor controller 196 and each of the drive systems 136, 138 to facilitate the communication and provision of power described herein.

In any event, the motor controller 196 communicates with the electronic control system 18 (or another component of the RCGS) via the bus interface and is configured to, among other things receive and execute motor control commands issued by the electronic control system 18 for controlling the movement of the respective motors 158, 168 of the drive systems 136, 138. Thus, in an exemplary embodiment, a user may input a command relating to a particular desired movement of the medical device 44 (e.g., rotation or deflection in a certain direction) via the input control system 16. The electronic control system 18 may translate or interpret the command, and then issue motor control commands to the motor controller 196, which then controls the appropriate motors 158, 168 in the appropriate way to effectuate or carry out the desired movement of the medical device 44. In an exemplary embodiment, the motor controller 196 is mounted on the mounting plate 132 of the manipulation base, though the present disclosure is not meant to be so limited.

As described above, in an exemplary embodiment the drive systems 138 each comprise a force sensor 190, such as, for example a strain gauge, coupled to the driven member 176. The strain gauge 190 is configured to measure the actuation forces being applied by the drive system 138 to the drive interface 64, and therefore, the tension of the steering wire 76 corresponding thereto. The strain gauge 190 is electrically coupled to the motor controller 196, the electronic control system 18, or both, and is configured to communicate the measured force being applied to the drive interface 64, and therefore, the corresponding steering wire 76. One purpose of employing a force sensor is to ensure that at least a minimum contact force between the driven member 176 and the drive interface 64 is maintained. More particularly, in certain instances it may be beneficial to maintain a minimum tension on all steering wires 76, even when such a steering wire 76 (and the slider block 61 corresponding thereto) is reactively translating in the distal direction, as was described above. Such minimal tension can help ensure that no undesirable measure of slack is created in any steering wire 76 that could potentially cause an unresponsive state (even if only momentarily) during a transition from a motion in one direction to motion in another direction. Accordingly, by incorporating the force sensor 190 in the manner set forth herein, the slider blocks 61 can be allowed to freely retract yet avoid contact latencies.

Thus, through the motor controller 196, each driven member 176 can be controllably positioned such that a minimal contact force between the driven member 176 and the corresponding drive interface 64, and therefore, the slider block 61, is always maintained. This ensures that all passive steering wires 76 (i.e., those not being actively tensioned) are maintained in a "ready state" yet are not significantly impeded (i.e., the slider blocks 61 corresponding to the passive steering wires 76 can still retract).

While the description above has been thus far with respect to the force sensor 190 comprising a force sensor that is attached to the driven member 176, the present disclosure is not meant to be so limited. Rather, in other exemplary embodiments, the force sensor 190 may be disposed within the shaft of the medical device 44 at or near the distal end thereof. In another exemplary embodiment, the force sensor 190 may comprise a motor current sensor that is electrically connected to the motor 168 of the drive system 138. In such an embodiment, the motor current sensor is configured to measure the current drawn by the motor 168 to thereby measure the actuation forces being applied by the drive system 138 to the drive interface 64, and therefore, the tension of the steering wire 76 corresponding thereto. In any event, and as with embodiment described above wherein the force sensor 190 comprises, for example, a strain gauge, and for the same purposes, the force sensor disposed within the shaft of the medical device 44 or the motor current sensor may be electrically coupled to the motor controller 196, the electronic control system 18, or both, either directly or indirectly (e.g., through the commutator 140, in the instance where the force sensor is disposed within the medical device 44, for example) and is configured to communicate the measured force being applied to the corresponding steering wire 76. In at least certain instances, the force sensor 190 provides a suitable way to perform mechanically isolated force sensing that minimizes external friction and forces, and therefore, provides a precise and accurate measurement of the force being applied to the corresponding steering wires 76.

As illustrated in FIG. 7, in an exemplary embodiment, the manipulation base 38 further comprises a housing 198 within which the drive systems 131, 138 and, in certain instances, other components of the manipulation base 38 are housed. The purpose of the housing 198 is to shield the medical device 44 and other components disposed in a sterile field that is external to the housing 198 (e.g., the patient table, drapes, the patient, etc.) from contaminants, and therefore, the help maintain sterility. In the embodiment illustrated in FIG. 7, the housing includes a first portion comprised of the mounting plate 132, and a second portion 200 that is detachably coupled with the mounting plate 132. In exemplary embodiment, the second portion 200 is formed of plastic, though the present disclosure is not meant to be so limited. The first and second portions of the housing 198 may be detachably coupled together using any number of techniques known in the art, including, but not limited to, those described elsewhere herein.

As illustrated in FIGS. 7 and 8, and as briefly described above, in an exemplary embodiment, the manipulation base 38 may further comprise a commutator 140. The commutator 140 is mounted on the mounting plate 132 on the same side that the cartridge 36 is attached to and has an housing 202 (best shown in FIG. 7) and a rotatable shaft 204 protruding therefrom. The commutator 140 is positioned on the mounting plate 132 in such a manner that when the cartridge 36 is attached to the mounting plate 132, the shaft 204 of the commutator 140 protrudes towards the cartridge 36 and is arranged coaxially with the opening 56 in the cartridge housing 40 and the port 66 of the rotatable assembly 42 to allow an electrical connector disposed at the distal end of the shaft 204 to be coupled with the electrical connector of the port 66. Accordingly, the commutator 140 has an electrical connector disposed at the end of the shaft 204 that is complementary to that of the port 66. As is known in the art, the input shaft 204 is configured to rotate such that as the rotatable assembly 42 of the cartridge 36 rotates, the shaft 204 also rotates without impeding the rotation of the rotatable assembly 42. Further, in an exemplary embodiment, the input shaft 204 is spring-loaded such that it can be pushed in towards the housing 202 to allow the cartridge 36 to be attached to the mounting plate 132, and then released to cause the shaft 204 to extend and be coupled to the port 66.

As illustrated in FIG. 8, the commutator 204 further comprises an electrical port 206. The electrical port 206 comprises an electrical connector configured to be electrically coupled with a complementary electrical connector of an electrical cable. For example, the port 206 may comprise a male plug connector having a plurality of pin contacts that is configured to be mated with a female receptacle connector having a plurality of socket contacts, or vice versa. The port 206 is electrically connected to the electrical connector of the shaft 204, and provides a means by which electrical signals acquired or generated by sensors 74 of the medical device 44 can be communicated to other components of the RCGS 10. More particularly, because the lead wires of sensors 74 are electrically coupled to the port 66, the port 66 is electrically coupled to the electrical connector of the commutator shaft 204, and the electrical connector of the commutator shaft 204 is electrically connected to the port 206, the electrical signals from the sensors 74 may be communicated to other components of the RCGS 10 through the commutator 140.

With reference to FIG. 2, in addition to the cartridge 36 and the manipulation base 38, in an exemplary embodiment, the drive head assembly 34 further comprises a sterility barrier 208 disposed between the base plate 48 of the cartridge 36 and the mounting plate 132 of the manipulation base 38. The purpose of the sterility barrier 208 is to shield the components of the cartridge 36, and other components disposed in a sterile field that is external to the cartridge outer housing 40 and the manipulation base housing 198, from contaminants, and therefore, help maintain the sterility of the medical device 44 and the sterile field. In an exemplary embodiment, the sterility barrier 208 is formed of polyethylene. In another exemplary embodiment, the barrier 208 is formed of polycarbonate. It will be appreciated that while only those materials set forth above have been specifically identified, in other exemplary embodiments the barrier 208 may be formed of materials or combinations of materials in addition to or other than those identified herein, and such embodiments remain within the spirit and scope of the present disclosure.

In an exemplary embodiment, in order to permit the engagements between the drive systems 136, 138 of the manipulation base 38 and the drive interfaces 62, 64 of the cartridge 36 described above, the barrier 208 has the same "layout" as that of the base plate 48 and mounting plate 132. More particularly, in such an embodiment the barrier 208 has the same number and arrangement of apertures or slots disposed therein as the base plate 48 and mounting plate 132. Similarly, the barrier 208 will further include the necessary apertures therein to allow for the cartridge 36 to be attached to the manipulation base 38. In an exemplary embodiment, the barrier 208 may be part of a larger bag assembly that may encapsulate the entire drive assembly 34, or one or the other of the cartridge 36 and drive assembly 48.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, all directional references (e.g., top and bottom) are only used for identification purposes to aid the reader's understanding of the present invention, and do not create limitations, particularly as to the position, orientation, or use of the invention. Further, the terms electrically connected and in communication are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

What is claimed is:

1. A medical device cartridge for use in a robotically controlled medical device guidance system, comprising:
    an outer housing; and
    a rotatable medical device assembly disposed within said outer housing, said rotatable medical device assembly comprising:
        an elongate medical device having a proximal end and a distal end;
        an inner housing having a first end, a second end, and a longitudinal axis extending therethrough, wherein said proximal end of said elongate medical device is disposed within said inner housing and said outer housing, and said inner housing further comprises an opening disposed in said first end thereof through which said elongate medical device extends outwardly from said inner housing in an axial direction relative to said longitudinal axis; and
        a drive interface coupled with said inner housing and configured to be operatively engaged with a drive system of a manipulation base in the robotically controlled medical device guidance system to impart rotational movement onto said rotatable medical device assembly about said longitudinal axis of said housing whereby said inner housing rotates relative to said outer housing;
    wherein said outer housing and said rotatable medical device assembly are configured for coextensive longitudinal movement along said longitudinal axis by a manipulator assembly to effect longitudinal movement of said elongate medical device.

2. The medical device cartridge of claim 1 wherein said outer housing comprises:
    a first portion having an opening therein that is coaxially arranged with said opening in said housing of said rotatable medical device assembly such that said elongate medical device extends outwardly from said outer housing; and
    a second portion comprising a base plate configured to permit said medical device cartridge to be removably attached to said manipulation base and having at least one aperture therein configured to permit the operative engagement of said drive interface with said drive system of said manipulation base.

3. The medical device cartridge of claim 1, wherein said drive interface is configured to be operatively engaged with said drive system of said manipulation base that is axially-arranged with said rotatable medical device assembly relative to said longitudinal axis of said housing thereof.

4. The medical device cartridge of claim 1 wherein said drive interface is configured to be operatively engaged with said drive system of said manipulation base that is disposed below said rotatable medical device assembly.

5. The medical device cartridge of claim 1, wherein said drive interface is a first drive interface configured to be operatively engaged with a first drive system of said manipulation base, and said elongate medical device comprises at least one steering wire, and further wherein said rotatable medical assembly further comprises:
- a control member disposed within said inner housing thereof and rigidly coupled with said steering wire of said elongate medical device, said control member configured for translational movement relative to said longitudinal axis of said housing; and
- a second drive interface coupled with said control member and configured to be operatively engaged with a second drive system of said manipulation base to impart translational movement onto said control member.

6. The medical device cartridge of claim 5 wherein said housing of said rotatable medical device assembly includes an axially extending slot therein, and said control member includes a pin extending therefrom in a radial direction relative to said longitudinal axis of said housing, and further wherein said pin is disposed and configured for travel within said slot in an axial direction relative to said longitudinal axis, and said second drive interface is coupled with said pin.

7. The medical device cartridge of claim 5, wherein said control member of said rotatable medical device assembly is a first control member and said steering wire coupled thereto is a first steering wire, and further wherein:
- said rotatable medical device assembly further comprises a second control member disposed within said housing and rigidly coupled to a second steering wire of said elongate medical device, said second control member configured for translational movement relative to said longitudinal axis of said housing; and
- said rotatable medical device assembly further comprises a third drive interface coupled with said second control member and configured to be operatively engaged with a third drive system of said manipulation base to impart translational movement onto said second control member.

8. The medical device cartridge of claim 7 wherein said housing of said rotatable medical device assembly includes an axially extending slot therein, and said second control member includes a pin extending therefrom in a radial direction relative to said longitudinal axis of said housing, and further wherein said pin is disposed and configured for travel within said slot in an axial direction relative to said longitudinal axis, and said third drive interface is coupled with said pin.

9. The medical device cartridge of claim 1 wherein said elongate medical device comprises a shaft and a force sensor disposed in said shaft, said force sensor configured to sense the force applied by said drive system onto said drive interface.

10. The medical device cartridge of claim 1, wherein said outer housing is configured to shield components disposed in a field external to said outer housing from contaminants.

* * * * *